United States Patent
Sur

(10) Patent No.: US 12,232,538 B2
(45) Date of Patent: *Feb. 25, 2025

(54) ARTIFICIAL INTELLIGENCE IN AN AEROSOL DELIVERY DEVICE

(71) Applicant: RAI STRATEGIC HOLDINGS, INC., Winston-Salem, NC (US)

(72) Inventor: Rajesh Sur, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/320,759

(22) Filed: May 19, 2023

(65) Prior Publication Data

US 2023/0292845 A1 Sep. 21, 2023

Related U.S. Application Data

(63) Continuation of application No. 16/394,737, filed on Apr. 25, 2019, now Pat. No. 11,690,405.

(51) Int. Cl.
*A24F 47/00* (2020.01)
*A24F 40/50* (2020.01)
(Continued)

(52) U.S. Cl.
CPC ............ *A24F 40/50* (2020.01); *G01C 22/006* (2013.01); *G06F 1/3206* (2013.01);
(Continued)

(58) Field of Classification Search
CPC ...... A24F 47/008; G06F 1/3206; G06F 21/32; G06K 9/00221; G06K 9/00335;
(Continued)

(56) References Cited

U.S. PATENT DOCUMENTS

| | | | |
|---|---|---|---|
| 2,057,353 | A | 10/1936 | Whittemore, Jr. |
| 2,104,266 | A | 1/1938 | Mccormick |

(Continued)

FOREIGN PATENT DOCUMENTS

| | | |
|---|---|---|
| CN | 1541577 A | 11/2004 |
| CN | 2719043 Y | 8/2005 |

(Continued)

OTHER PUBLICATIONS

"Getting started with MotionGR real-time gesture recognition library in X-CUBE-MEMS1 expansion for STM32Cube", ST Microelectronics, 2018, pp. 1-16.
(Continued)

*Primary Examiner* — Muthuswamy G Manoharan
(74) *Attorney, Agent, or Firm* — Womble Bond Dickinson (US) LLP

(57) ABSTRACT

An aerosol delivery device is provided that includes sensor(s) to produce measurements of properties during use of the device, and processing circuitry to record data for a plurality of uses of the device, for each use of which the data includes the measurements of the properties. The processing circuitry is configured to build a machine learning model to predict a target variable, using a machine learning algorithm, at least one feature selected from the properties, and a training set produced from the measurements of the properties. The processing circuitry is configured to then deploy the machine learning model to predict the target variable, and control at least one functional element of the device based thereon. The device may also verify authorization of an attempted user to alter a locked state of the device based on the verifying of the attempted user.

35 Claims, 8 Drawing Sheets

(51) Int. Cl.

| | | |
|---|---|---|
| *G01C 22/00* | (2006.01) | |
| *G06F 1/3206* | (2019.01) | |
| *G06F 18/214* | (2023.01) | |
| *G06F 21/32* | (2013.01) | |
| *G06K 9/00* | (2022.01) | |
| *G06K 9/62* | (2022.01) | |
| *G06N 5/00* | (2023.01) | |
| *G06N 20/00* | (2019.01) | |
| *G06N 20/10* | (2019.01) | |
| *G06N 20/20* | (2019.01) | |
| *G06V 40/16* | (2022.01) | |
| *G06V 40/20* | (2022.01) | |
| *H04L 9/06* | (2006.01) | |
| *H04W 4/02* | (2018.01) | |
| *H04W 4/80* | (2018.01) | |
| *H04L 9/00* | (2022.01) | |

(52) U.S. Cl.
CPC ............. *G06F 18/214* (2023.01); *G06N 5/00* (2013.01); *G06N 20/00* (2019.01); *G06N 20/10* (2019.01); *G06N 20/20* (2019.01); *G06V 40/16* (2022.01); *G06V 40/20* (2022.01); *H04W 4/027* (2013.01); *H04W 4/80* (2018.02); *H04L 9/50* (2022.05)

(58) Field of Classification Search
CPC ................ G06K 9/6256; G01C 22/006; H04L 9/0643; H04W 4/027; H04W 4/80
See application file for complete search history.

(56) References Cited

U.S. PATENT DOCUMENTS

| | | | |
|---|---|---|---|
| 3,200,819 | A | 8/1965 | Gilbert |
| 4,922,901 | A | 5/1990 | Brooks et al. |
| 5,060,671 | A | 10/1991 | Counts et al. |
| 5,093,894 | A | 3/1992 | Deevi et al. |
| 5,261,424 | A | 11/1993 | Sprinkel, Jr. |
| 5,388,574 | A | 2/1995 | Ingebrethsen |
| 5,530,225 | A | 6/1996 | Hajaligol |
| 5,687,746 | A | 11/1997 | Rose et al. |
| 5,726,421 | A | 3/1998 | Fleischhauer et al. |
| 5,865,185 | A | 2/1999 | Collins et al. |
| 5,894,841 | A | 4/1999 | Voges |
| 6,125,853 | A | 10/2000 | Susa et al. |
| 6,155,268 | A | 12/2000 | Takeuchi |
| 7,117,867 | B2 | 10/2006 | Cox et al. |
| 7,832,410 | B2 | 11/2010 | Hon |
| 8,314,591 | B2 | 11/2012 | Terry et al. |
| 8,365,742 | B2 | 2/2013 | Hon |
| 8,499,766 | B1 | 8/2013 | Newton |
| 8,577,122 | B2 | 11/2013 | Czarnotta et al. |
| 8,820,330 | B2 | 9/2014 | Bellinger et al. |
| 9,271,525 | B2 | 3/2016 | Liu |
| 9,532,604 | B2 | 1/2017 | Conley et al. |
| 9,642,317 | B2 | 5/2017 | Lewis et al. |
| 9,675,114 | B2 | 6/2017 | Timmermans |
| 9,756,878 | B2 | 9/2017 | Liu |
| 9,943,116 | B2 | 4/2018 | Cameron et al. |
| 9,955,728 | B2 | 5/2018 | Liu |
| 9,980,519 | B2 | 5/2018 | Kiang |
| 9,981,532 | B2 | 5/2018 | Blackley |
| 9,999,260 | B2 | 6/2018 | Memari et al. |
| 10,039,327 | B2 | 8/2018 | Cameron |
| 10,058,122 | B2 | 8/2018 | Steingraber et al. |
| 10,088,464 | B2 | 10/2018 | Blackley |
| 10,117,464 | B2 | 11/2018 | Liu |
| 10,123,565 | B2 | 11/2018 | Xiang |
| 10,127,741 | B2 | 11/2018 | Cameron et al. |
| 2005/0016550 | A1 | 1/2005 | Katase |
| 2006/0190419 | A1 | 8/2006 | Bunn et al. |
| 2006/0196518 | A1 | 9/2006 | Hon |
| 2008/0092912 | A1 | 4/2008 | Robinson et al. |
| 2009/0095311 | A1 | 4/2009 | Han |
| 2009/0126745 | A1 | 5/2009 | Hon |
| 2009/0188490 | A1 | 7/2009 | Han |
| 2009/0272379 | A1 | 11/2009 | Thorens et al. |
| 2011/0094523 | A1 | 4/2011 | Thorens et al. |
| 2011/0126848 | A1 | 6/2011 | Zuber et al. |
| 2011/0155718 | A1 | 6/2011 | Greim et al. |
| 2011/0168194 | A1 | 7/2011 | Hon |
| 2011/0265806 | A1 | 11/2011 | Alarcon et al. |
| 2011/0290248 | A1 | 12/2011 | Schennum |
| 2012/0111347 | A1 | 5/2012 | Hon |
| 2012/0260927 | A1 | 10/2012 | Liu |
| 2012/0279512 | A1 | 11/2012 | Hon |
| 2013/0037041 | A1 | 2/2013 | Worm et al. |
| 2013/0056013 | A1 | 3/2013 | Terry et al. |
| 2013/0183749 | A1 | 7/2013 | Aamodt et al. |
| 2013/0306084 | A1 | 11/2013 | Flick |
| 2013/0340775 | A1 | 12/2013 | Juster et al. |
| 2014/0000638 | A1 | 1/2014 | Sebastian et al. |
| 2014/0060554 | A1 | 3/2014 | Collett et al. |
| 2014/0060555 | A1 | 3/2014 | Chang et al. |
| 2014/0096781 | A1 | 4/2014 | Sears et al. |
| 2014/0096782 | A1 | 4/2014 | Ampolini et al. |
| 2014/0107815 | A1 | 4/2014 | LaMothe |
| 2014/0209105 | A1 | 7/2014 | Sears et al. |
| 2014/0253144 | A1 | 9/2014 | Novak, III et al. |
| 2014/0261408 | A1 | 9/2014 | DePiano et al. |
| 2014/0261486 | A1 | 9/2014 | Potter et al. |
| 2014/0261487 | A1 | 9/2014 | Chapman et al. |
| 2014/0261495 | A1 | 9/2014 | Novak et al. |
| 2014/0270727 | A1 | 9/2014 | Ampolini et al. |
| 2014/0270729 | A1 | 9/2014 | DePiano et al. |
| 2014/0270730 | A1 | 9/2014 | DePiano et al. |
| 2014/0278250 | A1 | 9/2014 | Smith et al. |
| 2015/0066429 | A1 | 3/2015 | Nielsen et al. |
| 2015/0142387 | A1 | 5/2015 | Alarcon et al. |
| 2015/0173124 | A1 | 6/2015 | Qiu |
| 2015/0181945 | A1 | 7/2015 | Tremblay |
| 2015/0196057 | A1 | 7/2015 | Wu |
| 2015/0223521 | A1* | 8/2015 | Menting ................ A24F 40/50 131/273 |
| 2015/0282527 | A1 | 10/2015 | Henry, Jr. |
| 2015/0297778 | A1 | 10/2015 | Conroy et al. |
| 2016/0089508 | A1 | 3/2016 | Smith et al. |
| 2016/0143361 | A1 | 5/2016 | Juster et al. |
| 2016/0158782 | A1* | 6/2016 | Henry, Jr. ............... A24F 40/51 700/275 |
| 2016/0171164 | A1 | 6/2016 | Kinzer |
| 2016/0278435 | A1 | 9/2016 | Choukroun et al. |
| 2016/0321879 | A1 | 11/2016 | Oh et al. |
| 2016/0338407 | A1 | 11/2016 | Kerdemelidis |
| 2016/0371437 | A1 | 12/2016 | Alarcon et al. |
| 2017/0014582 | A1 | 1/2017 | Skoda |
| 2017/0042247 | A1 | 2/2017 | Xiang |
| 2017/0091853 | A1 | 3/2017 | Cameron |
| 2017/0108840 | A1 | 4/2017 | Hawes et al. |
| 2017/0135405 | A1 | 5/2017 | Reevell |
| 2017/0135407 | A1 | 5/2017 | Cameron |
| 2017/0136193 | A1 | 5/2017 | Cameron |
| 2017/0136301 | A1 | 5/2017 | Cameron |
| 2017/0182267 | A1 | 6/2017 | Cameron |
| 2017/0303590 | A1 | 10/2017 | Cameron et al. |
| 2017/0303592 | A1 | 10/2017 | Cameron et al. |
| 2017/0308889 | A1 | 10/2017 | Cameron et al. |
| 2017/0318861 | A1* | 11/2017 | Thorens ................ A24F 40/53 |
| 2017/0368273 | A1 | 12/2017 | Rubin |
| 2018/0027872 | A1 | 2/2018 | Galaviz, Jr. |
| 2018/0043114 | A1 | 2/2018 | Bowen et al. |
| 2018/0047553 | A1 | 2/2018 | Richardson et al. |
| 2018/0121706 | A1 | 5/2018 | Dante et al. |
| 2018/0132528 | A1 | 5/2018 | Sur et al. |
| 2018/0213846 | A1 | 8/2018 | Wendt Thevenaz et al. |
| 2018/0221604 | A1 | 8/2018 | Trzecieski |
| 2018/0263288 | A1 | 9/2018 | Goldstein et al. |
| 2018/0270311 | A1 | 9/2018 | Baker et al. |
| 2018/0271155 | A1 | 9/2018 | Baker et al. |
| 2018/0304032 | A9 | 10/2018 | Trzecieski |
| 2019/0008209 | A1 | 1/2019 | Bilat |
| 2019/0014819 | A1 | 1/2019 | Sur |

(56) References Cited

U.S. PATENT DOCUMENTS

| | | | |
|---|---|---|---|
| 2019/0021397 A1 | 1/2019 | Zhang et al. | |
| 2019/0027240 A1 | 1/2019 | Davidson et al. | |
| 2019/0087302 A1 | 3/2019 | Smith et al. | |
| 2019/0289915 A1* | 9/2019 | Heidl | G06F 3/016 |
| 2019/0387796 A1 | 12/2019 | Cohen | |
| 2020/0000143 A1 | 1/2020 | Anderson et al. | |
| 2020/0352249 A1* | 11/2020 | Achtien | A61M 15/0066 |
| 2020/0376208 A1 | 12/2020 | Spencer et al. | |
| 2021/0011446 A1* | 1/2021 | Anderson | G05B 19/042 |

FOREIGN PATENT DOCUMENTS

| | | | | |
|---|---|---|---|---|
| CN | 201379072 Y | | 1/2010 | |
| CN | 107205481 A | | 9/2017 | |
| CN | 109152425 A | | 1/2019 | |
| EP | 3681009 | | 7/2020 | |
| FR | 3049133 A1 | | 9/2017 | |
| GB | 2469850 A | | 11/2010 | |
| GB | 2570439 | | 7/2019 | |
| GB | 2570439 A | * | 7/2019 | A24D 1/00 |
| KR | 10-2010-0097807 A | | 9/2010 | |
| KR | 10-2016-0130143 A | | 11/2016 | |
| RU | 2625932 | | 7/2017 | |
| RU | 2677158 | | 1/2019 | |
| WO | 2003034847 | | 5/2003 | |
| WO | 2004080216 A1 | | 9/2004 | |
| WO | 2005099494 A1 | | 10/2005 | |
| WO | 2007131449 A1 | | 11/2007 | |
| WO | 2014199233 | | 12/2014 | |
| WO | WO-2014199233 A2 | * | 12/2014 | A24B 15/167 |
| WO | WO 2015/138589 | | 9/2015 | |
| WO | WO-2017055793 A1 | * | 4/2017 | A24B 15/167 |
| WO | WO 2017/205692 | | 11/2017 | |
| WO | WO 2018/098371 | | 5/2018 | |
| WO | WO 2018/202403 A1 | | 11/2018 | |
| WO | WO 2019/016681 | | 1/2019 | |
| WO | WO 2019/030000 A1 | | 2/2019 | |
| WO | 2019105812 | | 6/2019 | |
| WO | WO-2019105812 A1 | * | 6/2019 | A24F 40/05 |
| WO | 2019171017 | | 9/2019 | |
| WO | 2019175810 | | 9/2019 | |
| WO | WO-2019171017 A1 | * | 9/2019 | A24B 15/243 |

OTHER PUBLICATIONS

"Getting started with MotionCP real-time carry position library in X-CUBE-MEMS1 expansion for STM32Cube", ST Microelectronics, Mar. 2018, pp. 1-17.

"Getting started with MotionAR activity recognition library in X-CUBE-MEMS1 expansion for STM32Cube", ST Microelectronics, Mar. 2018, pp. 1-16.

Perez, S., "Juul says it will use technology to help you quit e-cigarettes, too", 2018, TechCrunch, received Feb. 22, 2019 from https://techcrunch.com/2018/09/05/juul-says-it-will-use-technology-to-help-you-quit-e-cigarettes-too/.

"Getting started with the FP-AUD-BVLINK1 STM32 ODE function pack based on half-duplex voice streaming over BLE", ST Microelectronics, Jun. 2017, pp. 1-60.

"Getting started with AcousticBF real-time beam forming middleware", ST Microelectronics, May 2017, pp. 1-16.

International Search Report from the corresponding International Application No. PCT/IB2020/053823, dated Jul. 21, 2020.

Third Office Action issued Sep. 3, 2024, in corresponding Chinese Application No. 202080031371.X.

Notice on Grant of Patent Right issued Nov. 29, 2024, in corresponding Chinese Application No. 202080031371.X.

Notice of Allowance issued Oct. 22, 2024, in corresponding Japanese application No. 2021-563039.

* cited by examiner

FIG. 10

ARTIFICIAL INTELLIGENCE IN AN AEROSOL DELIVERY DEVICE

CROSS REFERENCE TO RELATED APPLICATIONS

This application is a continuation of U.S. application Ser. No. 16/394,737, filed Apr. 25, 2019, which is hereby incorporated herein in its entirety by reference.

TECHNOLOGICAL FIELD

The present disclosure relates to aerosol delivery devices such as smoking articles that produce aerosol. The smoking articles may be configured to heat or otherwise dispense an aerosol precursor or otherwise produce an aerosol from an aerosol precursor, which may incorporate materials that may be made or derived from tobacco or otherwise incorporate tobacco, the precursor being capable of forming an inhalable substance for human consumption.

BACKGROUND

Many smoking articles have been proposed through the years as improvements upon, or alternatives to, smoking products based upon combusting tobacco. Some example alternatives have included devices wherein a solid or liquid fuel is combusted to transfer heat to tobacco or wherein a chemical reaction is used to provide such heat source. Additional example alternatives use electrical energy to heat tobacco and/or other aerosol generating substrate materials, such as described in U.S. Pat. No. 9,078,473 to Worm et al., which is incorporated herein by reference.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. Pub. No. 2009/0095311 to Hon; U.S. Pat. Pub. Nos. 2006/0196518, 2009/0126745, and 2009/0188490 to Hon; U.S. Pat. Pub. No. 2009/0272379 to Thorens et al.; U.S. Pat. Pub. Nos. 2009/0260641 and 2009/0260642 to Monsees et al.; U.S. Pat. Pub. Nos. 2008/0149118 and 2010/0024834 to Oglesby et al.; U.S. Pat. Pub. No. 2010/0307518 to Wang; and WO 2010/091593 to Hon, which are incorporated herein by reference.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Fontem Ventures B.V; COHITA™ COLIBRI™, ELITE CLASSIC™, MAGNUM™, PHANTOM™ and SENSE™ by EPUFFER® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™, HENDU™, JET™ MAXXQ™, PINK™ and PITBULL™ by SMOKE STIK®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; MISTIC MENTHOL product by Mistic Ecigs; the VYPE product by CN Creative Ltd; IQOS™ by Philip Morris International; GLO™ by British American Tobacco; MARK TEN products by Nu Mark LLC; and the JUUL product by Juul Labs, Inc. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; and SOUTH BEACH SMOKE™.

However, it may be desirable to provide aerosol delivery devices with improved electronics such as may extend usability of the devices.

SUMMARY

The present disclosure relates to aerosol delivery devices configured to produce aerosol and which aerosol delivery devices, in some implementations, may be referred to as electronic cigarettes, heat-not-burn cigarettes (or devices), or no-heat-no-burn devices. The present disclosure includes, without limitation, the following example implementations.

Some example implementations provide an aerosol delivery device comprising: a housing structured to retain an aerosol precursor composition; at least one sensor configured to produce measurements of properties during use of the aerosol delivery device; a power source; an aerosol production component configured to produce an aerosol from the aerosol precursor composition; and a control component including processing circuitry configured to switchably connect the power source to a load including the aerosol production component and thereby power the aerosol production component, record data for a plurality of uses of the aerosol delivery device, for each use of which the data includes the measurements of the properties, build a machine learning model to predict a target variable, the machine learning model built using a machine learning algorithm, at least one feature selected from the properties, and a training set produced from the measurements of the properties, deploy the machine learning model to predict the target variable, and control at least one functional element of the aerosol delivery device based thereon, and verify that an attempted user is authorized to use the aerosol delivery device, wherein the processing circuitry being configured to control the at least one functional element includes being configured to alter a locked state of the aerosol delivery device based on the verifying of the attempted user.

In some example implementations of the aerosol delivery device of any preceding example implementation, or any combination of any preceding example implementations, the aerosol delivery device further comprises a camera system including a digital camera configured to capture an image of a face of the attempted user of the aerosol delivery device, wherein the processing circuitry is configured to perform a facial recognition using the image to verify the attempted user is authorized to use the aerosol delivery device, and the processing circuitry being configured to control the at least one functional element includes being configured to alter a locked state of the aerosol delivery device based on the verifying of the attempted user.

In some example implementations of the aerosol delivery device of any preceding example implementation, or any combination of any preceding example implementations, the plurality of uses of the aerosol delivery device includes respective user puffs each of which causes a flow of air through at least a portion of the housing, and is for user inhalation of the aerosol, and wherein the processing circuitry being configured to record the data for the plurality of uses includes being configured to record the measurements with times and durations of the respective user puffs, and the target variable is a user profile that depends on at least one of the properties, and the times and durations of the respective user puffs.

In some example implementations of the aerosol delivery device of any preceding example implementation, or any combination of any preceding example implementations, the user profile includes information that indicates a predicted period of non-use of the aerosol delivery device, and the processing circuitry being configured to control the at least one functional element includes being configured to cause the aerosol delivery device to enter a sleep mode during the predicted period of non-use.

In some example implementations of the aerosol delivery device of any preceding example implementation, or any combination of any preceding example implementations, the processing circuitry being configured to control the at least one functional element includes being configured to control power from the power source to the load including the aerosol production component based on the user profile.

In some example implementations of the aerosol delivery device of any preceding example implementation, or any combination of any preceding example implementations, the aerosol production component includes a plurality of meshes surrounded by piezoelectric or piezomagnetic material, the processing circuitry configured to selectively drive the piezoelectric or piezomagnetic material to vibrate and cause a discharge of components of the aerosol precursor composition through one or more of the meshes, and wherein the processing circuitry being configured to control power from the power source includes being configured to control power from the power source to selectively drive the piezoelectric or piezomagnetic material based on the user profile.

In some example implementations of the aerosol delivery device of any preceding example implementation, or any combination of any preceding example implementations, the at least one sensor includes a pressure sensor configured to produce measurements of pressure caused by the flow of air, and the at least one of the properties on which the user profile depends includes the measurements of pressure that are proportional to strength of the respective user puffs.

In some example implementations of the aerosol delivery device of any preceding example implementation, or any combination of any preceding example implementations, the at least one sensor includes a pressure sensor configured to produce measurements of pressure caused by the flow of air that are proportional to total particular matter (TPM) in the aerosol produced during the respective user puffs, and the at least one of the properties on which the user profile depends includes the measurements of pressure that are proportional to TPM in the aerosol produced during the respective user puffs.

In some example implementations of the aerosol delivery device of any preceding example implementation, or any combination of any preceding example implementations, the at least one sensor includes a current or voltage sensor configured to produce measurements of current through or voltage across the aerosol production component, and the processing circuitry is further configured to determine power dissipated by the aerosol production component during the respective user puffs based on the measurements of current through or voltage across the aerosol production component, and wherein the at least one of the properties on which the user profile depends includes the power dissipated by the aerosol production component during the respective user puffs.

In some example implementations of the aerosol delivery device of any preceding example implementation, or any combination of any preceding example implementations, the aerosol delivery device is usable with at least a plurality of aerosol precursor compositions, and the at least one sensor includes a reader configured to read machine-readable information from which the processing circuitry is configured to identify respective ones of the plurality of aerosol precursor compositions during the respective user puffs when the aerosol delivery device is used therewith, and wherein the user profile depends on at least the respective ones of the plurality of aerosol precursor compositions identified by the processing circuitry, and the times and durations of the respective user puffs when the aerosol delivery device is used therewith.

In some example implementations of the aerosol delivery device of any preceding example implementation, or any combination of any preceding example implementations, the aerosol production component is a plurality of aerosol production components configured to produce aerosol from the plurality of aerosol precursor compositions, and wherein the processing circuitry being configured to control the at least one functional element includes being configured to automatically select among the plurality of aerosol production components at different times based on the user profile.

In some example implementations of the aerosol delivery device of any preceding example implementation, or any combination of any preceding example implementations, the processing circuitry is further configured to predict depletion of a particular one of the plurality of aerosol precursor compositions based on the user profile, and wherein the aerosol delivery device further comprises a wireless communication interface, and the processing circuitry being configured to control the at least one function element includes being configured to communicate with a computing device or a service platform via the wireless communication interface to order an additional amount of the particular one of the plurality of aerosol precursor compositions.

In some example implementations of the aerosol delivery device of any preceding example implementation, or any combination of any preceding example implementations, the at least one sensor includes a position sensor configured to determine a geographic position of the aerosol delivery device, and the at least one of the properties on which the user profile depends includes the geographic position of the aerosol delivery device during the respective user puffs.

In some example implementations of the aerosol delivery device of any preceding example implementation, or any combination of any preceding example implementations, the aerosol delivery device further comprises a wireless communication interface via which the aerosol delivery device is configured to receive, from a second aerosol delivery device, second measurements of the properties during use of the second aerosol delivery device that includes respective second user puffs, and second times and durations of the respective second user puffs, wherein the processing circuitry is further configured to build and deploy a second machine learning model to predict a second target variable, the second machine learning model built using the machine learning algorithm, the at least one feature selected from the properties, and a second training set produced from the second measurements of the properties, the second target variable being a second user profile that depends on the at least one of the properties, and the second times and durations of the respective second user puffs.

In some example implementations of the aerosol delivery device of any preceding example implementation, or any combination of any preceding example implementations, the at least one sensor includes an accelerometer configured to produce measurements of acceleration of the aerosol delivery device, and the target variable is a logical activity of a user of the aerosol delivery device, and wherein the processing circuitry being configured to build the machine learning model includes being configured to build an activity detection model to predict the logical activity of the user, the activity detection model being built using the machine learning algorithm, the at least one feature that includes the acceleration, and the training set produced from the measurements of acceleration.

In some example implementations of the aerosol delivery device of any preceding example implementation, or any combination of any preceding example implementations, the at least one sensor includes an accelerometer configured to produce measurements of acceleration of the aerosol delivery device, and the target variable is a logical carry position of the aerosol delivery device, and wherein the processing circuitry being configured to build the machine learning model includes being configured to build a carry position detection model to predict the logical carry position of the aerosol delivery device, the carry position detection model being built using the machine learning algorithm, the at least one feature that includes the acceleration, and the training set produced from the measurements of acceleration.

In some example implementations of the aerosol delivery device of any preceding example implementation, or any combination of any preceding example implementations, the at least one sensor includes an accelerometer configured to produce measurements of acceleration of the aerosol delivery device, and the target variable is a gesture performed using the aerosol delivery device, and wherein the processing circuitry being configured to build the machine learning model includes being configured to build a gesture recognition model to predict the gesture, the gesture recognition model being built using the machine learning algorithm, the at least one feature that includes the acceleration, and the training set produced from the measurements of acceleration.

In some example implementations of the aerosol delivery device of any preceding example implementation, or any combination of any preceding example implementations, the at least one sensor includes microphones configured to produce measurements of audio from an audio source in an environment of the aerosol delivery device, and wherein the processing circuitry is further configured to create a virtual directional microphone having a beam pattern created from the measurements of audio, and that points in a direction of the audio source.

In some example implementations of the aerosol delivery device of any preceding example implementation, or any combination of any preceding example implementations, the aerosol delivery device further comprises a wireless communication interface, and wherein the processing circuitry is further configured to enable half-duplex Bluetooth Low Energy communication with a computing device via the wireless communication interface.

In some example implementations of the aerosol delivery device of any preceding example implementation, or any combination of any preceding example implementations, the at least one sensor includes a sensor configured to produce measurements of resistance of the aerosol precursor composition, and the target variable is a measure of quality of the aerosol precursor composition that is proportional to a resistivity of the aerosol precursor composition, and the resistivity is determinable from the measurements of resistance, and wherein the processing circuitry being configured to build the machine learning model includes being configured to build the machine learning model to predict the measure of quality of the aerosol precursor composition, the model being built using the machine learning algorithm, the at least one feature that includes the resistance of the aerosol precursor composition, and the training set produced from the measurements of resistance.

In some example implementations of the aerosol delivery device of any preceding example implementation, or any combination of any preceding example implementations, the power source is rechargeable, the data for the plurality of uses includes a count and frequency of recharges of the power source, and the target variable is a measure of life expectancy of the aerosol precursor composition or the power source that is proportional to the count and frequency of recharges of the power source, and wherein the processing circuitry being configured to build the machine learning model includes being configured to build the machine learning model to predict the measure of life expectancy of the aerosol precursor composition or the power source, the model being built using the machine learning algorithm, the at least one feature that includes the count and frequency of recharges of the power source, and the training set produced from the count and frequency of recharges.

In some example implementations of the aerosol delivery device of any preceding example implementation, or any combination of any preceding example implementations, the at least one sensor includes an accelerometer configured to produce measurements of acceleration of the aerosol delivery device, and the target variable is or is based on a measure of activity of a user of the aerosol delivery device that is proportional to a count of steps of the user, and the count of steps is determinable from the measurements of acceleration, and wherein the processing circuitry being configured to build the machine learning model includes being configured to build the machine learning model to predict the measure of activity of the user, the model being built using the machine learning algorithm, the at least one feature that includes the acceleration, and the training set produced from the measurements of acceleration.

In some example implementations of the aerosol delivery device of any preceding example implementation, or any combination of any preceding example implementations, the plurality of uses of the aerosol delivery device includes respective user puffs each of which causes a flow of air through at least a portion of the housing, and is for user inhalation of the aerosol, and wherein the processing circuitry being configured to record the data for the plurality of uses includes being configured to record the measurements with times and durations of the respective user puffs, and the target variable is a measure of health of the user, based on the measure of activity, and further based on a usage rate that depends on the times and durations of the respective user puffs.

In some example implementations of the aerosol delivery device of any preceding example implementation, or any combination of any preceding example implementations, the aerosol delivery device further comprises a wireless communication interface, wherein the processing circuitry being configured to control the at least one function element includes being configured to communicate the target variable to a service platform via the wireless communication interface, the service platform configured to electronically record the target variable on a blockchain.

In some example implementations of the aerosol delivery device of any preceding example implementation, or any combination of any preceding example implementations, the user profile includes or defines a puff profile of an authorized user of the aerosol delivery device, wherein the processing circuitry is configured to develop a use-specific puff profile of respective user puffs during a use of the aerosol delivery device, and compare the use-specific puff profile to the authorized user puff profile, and the processing circuitry being configured to control the at least one functional element includes being configured to enable continued use of the aerosol delivery device when the use-specific puff profile and authorized user puff profile match or have at least a threshold similarity, and being configured to lock the aerosol delivery device from continued use when the use-specific puff profile and authorized user puff profile do not match or have at least the threshold similarity.

In some example implementations of the aerosol delivery device of any preceding example implementation, or any combination of any preceding example implementations, the user profile includes or defines a threshold age of an authorized user associated with the authorized user puff profile, and the processing circuitry being configured to control the at least one functional element includes being configured to enable continued use of the aerosol delivery device when the use-specific puff profile indicates that the attempted user is at least the threshold age, and being configured to lock the aerosol delivery device from continued use when the use-specific puff profile indicates that the attempted user is not at least the threshold age.

In some example implementations of the aerosol delivery device of any preceding example implementation, or any combination of any preceding example implementations, the user profile includes information that indicates one or more predicted geographic areas of use or non-use of the aerosol delivery device, predicted based on the geographic positions of the aerosol delivery device during the user puffs, and the processing circuitry being configured to control the at least one functional element includes being configured to unlock the aerosol delivery device when the aerosol delivery device is located within a predicted geographic area of use, and being configured to lock the aerosol delivery device when the aerosol delivery device is located outside the predicted geographic area of use or is within a predicted geographic area of non-use.

In some example implementations of the aerosol delivery device of any preceding example implementation, or any combination of any preceding example implementations, the user profile includes information that indicates one or more predicted geographic areas of use or non-use of the aerosol delivery device, predicted based on the geographic positions of the aerosol delivery device during the user puffs, and the processing circuitry being configured to control the at least one functional element includes being configured to prepare the aerosol delivery device for use when approaching or within a predicted geographic area of use, wherein preparing includes restoring the aerosol delivery device from a sleep mode or activating components to which power is cut in the sleep mode, and being configured to cause the aerosol delivery device to enter the sleep mode when the aerosol delivery device exits or is located outside the predicted geographic area of use, or approaches or is within a predicted geographic area of non-use.

In some example implementations of the aerosol delivery device of any preceding example implementation, or any combination of any preceding example implementations, the user profile includes information that indicates one or more predicted geographic areas of modified use of the aerosol delivery device, predicted based on the geographic positions of the aerosol delivery device during the user puffs, and the processing circuitry being configured to control the at least one functional element includes being configured to cause the aerosol delivery device to adjust by increasing or decreasing a volume of aerosol produced by the aerosol delivery device when the aerosol delivery device is located within one of the predicted geographic area of modified use.

Some example implementations provide an aerosol delivery device comprising: an aerosol precursor composition; at least one sensor configured to produce measurements of properties during use of the aerosol delivery device; a power source; an aerosol production component configured to produce an aerosol from the aerosol precursor composition; and a control component including processing circuitry configured to: switchably connect the power source to a load including the aerosol production component and thereby power the aerosol production component, record data for a plurality of uses of the aerosol delivery device, for each use of which the data includes the measurements of the properties, build a machine learning model to predict a target variable, the machine learning model built using a machine learning algorithm, at least one feature selected from the properties, and a training set produced from the measurements of the properties, and deploy the machine learning model to predict the target variable, and control at least one functional element of the aerosol delivery device based thereon, wherein the processing circuitry being configured to record the data for the plurality of uses includes being configured to record the measurements with times and durations of the respective user puffs, and the target variable is a user profile that depends on at least one of the properties, and the times and durations of the respective user puffs, and wherein the user profile includes information that indicates a predicted period of non-use of the aerosol delivery device, and the processing circuitry being configured to control the at least one functional element includes being configured to cause the aerosol delivery device to enter a sleep mode during the predicted period of non-use.

Some example implementations provide an aerosol delivery device comprising: an aerosol precursor composition; at least one sensor configured to produce measurements of properties during use of the aerosol delivery device; a power source; an aerosol production component configured to produce an aerosol from the aerosol precursor composition; and a control component including processing circuitry configured to: switchably connect the power source to a load including the aerosol production component and thereby power the aerosol production component, record data for a plurality of uses of the aerosol delivery device, for each use of which the data includes the measurements of the properties, build a machine learning model to predict a target variable, the machine learning model built using a machine learning algorithm, at least one feature selected from the properties, and a training set produced from the measurements of the properties, and deploy the machine learning model to predict the target variable, and control at least one functional element of the aerosol delivery device based thereon, wherein the processing circuitry being configured to record the data for the plurality of uses includes being configured to record the measurements with times and durations of the respective user puffs, and the target variable is a user profile that depends on at least one of the properties, and the times and durations of the respective user puffs, and wherein the user profile includes or defines a puff profile of an authorized user of the aerosol delivery device, wherein the processing circuitry is configured to develop a use-specific puff profile of respective user puffs during a use of the aerosol delivery device, and compare the use-specific puff profile to the authorized user puff profile, and the processing circuitry being configured to control the at least one functional element includes being configured to enable continued use of the aerosol delivery device when the use-specific puff profile and authorized user puff profile match or have at least a threshold similarity, and being configured to lock the aerosol delivery device from continued use when the use-specific puff profile and authorized user puff profile do not match or have at least the threshold similarity.

Some example implementations provide an aerosol delivery device comprising: an aerosol precursor composition; at least one sensor configured to produce measurements of properties during use of the aerosol delivery device; a power source; an aerosol production component configured to produce an aerosol from the aerosol precursor composition; and a control component including processing circuitry configured to: switchably connect the power source to a load including the aerosol production component and thereby power the aerosol production component, record data for a plurality of uses of the aerosol delivery device, for each use of which the data includes the measurements of the properties, build a machine learning model to predict a target variable, the machine learning model built using a machine learning algorithm, at least one feature selected from the properties, and a training set produced from the measurements of the properties, and deploy the machine learning model to predict the target variable, and control at least one functional element of the aerosol delivery device based thereon, wherein the processing circuitry being configured to record the data for the plurality of uses includes being configured to record the measurements with times and durations of the respective user puffs, and the target variable is a user profile that depends on at least one of the properties, and the times and durations of the respective user puffs, and wherein the user profile includes or defines a threshold age of an authorized user associated with the authorized user puff profile, and the processing circuitry being configured to control the at least one functional element includes being configured to enable continued use of the aerosol delivery device when the use-specific puff profile indicates that the attempted user is at least the threshold age, and being configured to lock the aerosol delivery device from continued use when the use-specific puff profile indicates that the attempted user is not at least the threshold age.

Some example implementations provide an aerosol delivery device comprising: an aerosol precursor composition; at least one sensor configured to produce measurements of properties during use of the aerosol delivery device; a power source; an aerosol production component configured to produce an aerosol from the aerosol precursor composition; and a control component including processing circuitry configured to: switchably connect the power source to a load including the aerosol production component and thereby power the aerosol production component, record data for a plurality of uses of the aerosol delivery device, for each use of which the data includes the measurements of the properties, build a machine learning model to predict a target variable, the machine learning model built using a machine learning algorithm, at least one feature selected from the properties, and a training set produced from the measurements of the properties, and deploy the machine learning model to predict the target variable, and control at least one functional element of the aerosol delivery device based thereon, wherein the at least one sensor includes a position sensor configured to determine a geographic position of the aerosol delivery device, and the at least one of the properties on which the user profile depends includes the geographic position of the aerosol delivery device during the respective user puffs, and wherein the user profile includes information that indicates one or more predicted geographic areas of use or non-use of the aerosol delivery device, predicted based on the geographic positions of the aerosol delivery device during the user puffs, and the processing circuitry being configured to control the at least one functional element includes being configured to unlock the aerosol delivery device when the aerosol delivery device is located within a predicted geographic area of use, and being configured to lock the aerosol delivery device when the aerosol delivery device is located outside the predicted geographic area of use or is within a predicted geographic area of non-use.

Some example implementations provide an aerosol delivery device comprising: an aerosol precursor composition; at least one sensor configured to produce measurements of properties during use of the aerosol delivery device; a power source; an aerosol production component configured to produce an aerosol from the aerosol precursor composition; and a control component including processing circuitry configured to: switchably connect the power source to a load including the aerosol production component and thereby power the aerosol production component, record data for a plurality of uses of the aerosol delivery device, for each use of which the data includes the measurements of the properties, build a machine learning model to predict a target variable, the machine learning model built using a machine learning algorithm, at least one feature selected from the properties, and a training set produced from the measurements of the properties, and deploy the machine learning model to predict the target variable, and control at least one functional element of the aerosol delivery device based thereon, wherein the at least one sensor includes a position sensor configured to determine a geographic position of the aerosol delivery device, and the at least one of the properties on which the user profile depends includes the geographic position of the aerosol delivery device during the respective user puffs, and wherein the user profile includes information that indicates one or more predicted geographic areas of use or non-use of the aerosol delivery device, predicted based on the geographic positions of the aerosol delivery device during the user puffs, and the processing circuitry being configured to control the at least one functional element includes being configured to prepare the aerosol delivery device for use when approaching or within a predicted geographic area of use, wherein preparing includes restoring the aerosol delivery device from a sleep mode or activating components to which power is cut in the sleep mode, and being configured to cause the aerosol delivery device to enter the sleep mode when the aerosol delivery device exits or is located outside the predicted geographic area of use, or approaches or is within a predicted geographic area of non-use.

Some example implementations provide an aerosol delivery device comprising: an aerosol precursor composition; at least one sensor configured to produce measurements of properties during use of the aerosol delivery device; a power source; an aerosol production component configured to produce an aerosol from the aerosol precursor composition; and a control component including processing circuitry configured to: switchably connect the power source to a load including the aerosol production component and thereby power the aerosol production component, record data for a plurality of uses of the aerosol delivery device, for each use of which the data includes the measurements of the properties, build a machine learning model to predict a target variable, the machine learning model built using a machine learning algorithm, at least one feature selected from the properties, and a training set produced from the measurements of the properties, and deploy the machine learning model to predict the target variable, and control at least one functional element of the aerosol delivery device based thereon, wherein the at least one sensor includes a position sensor configured to determine a geographic position of the aerosol delivery device, and the at least one of the properties on which the user profile depends includes the geographic position of the aerosol delivery device during the respective user puffs, and wherein the user profile includes information that indicates one or more predicted geographic areas of modified use of the aerosol delivery device, predicted based on the geographic positions of the aerosol delivery device during the user puffs, and the processing circuitry being configured to control the at least one functional element includes being configured to cause the aerosol delivery device to adjust by increasing or decreasing a volume of aerosol produced by the aerosol delivery device when the aerosol delivery device is located within one of the predicted geographic area of modified use.

These and other features, aspects, and advantages of the present disclosure will be apparent from a reading of the following detailed description together with the accompanying figures, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

It will therefore be appreciated that this Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying figures which illustrate, by way of example, the principles of some described example implementations.

BRIEF DESCRIPTION OF THE FIGURES

Figure 1:
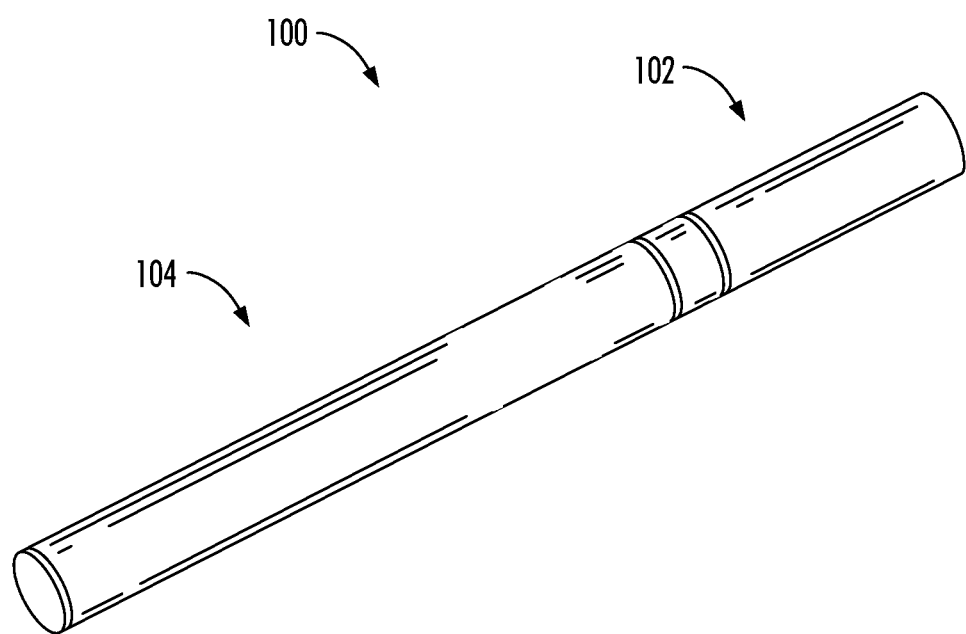
Figure 2:
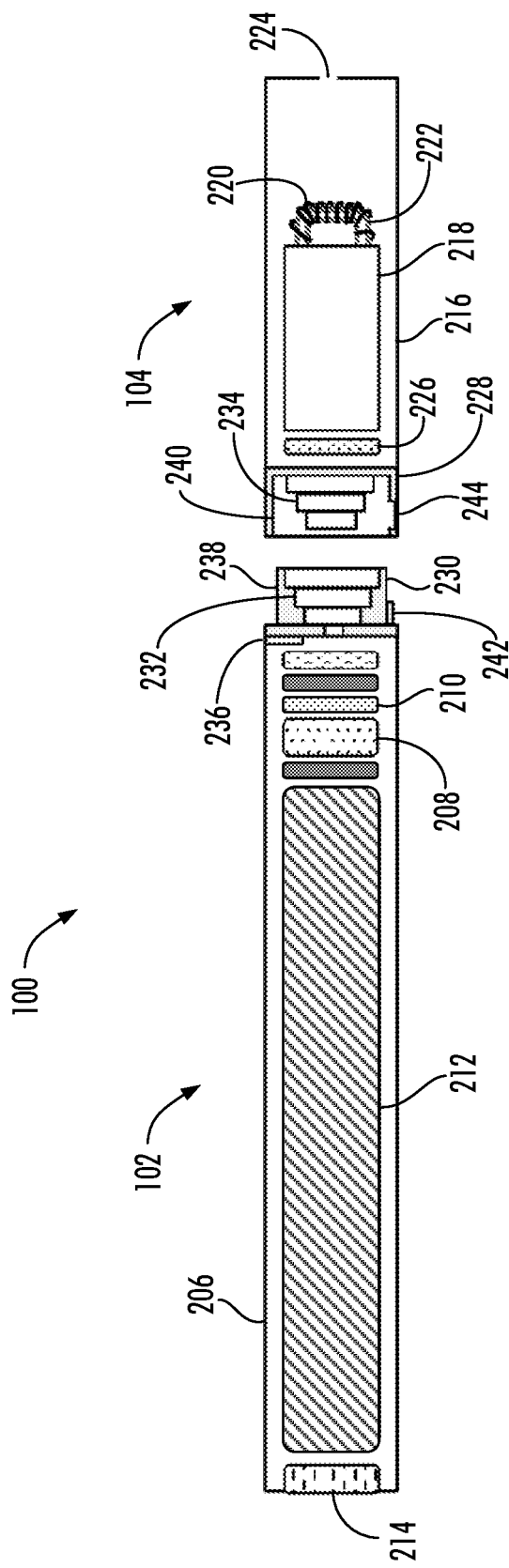
Figure 3:
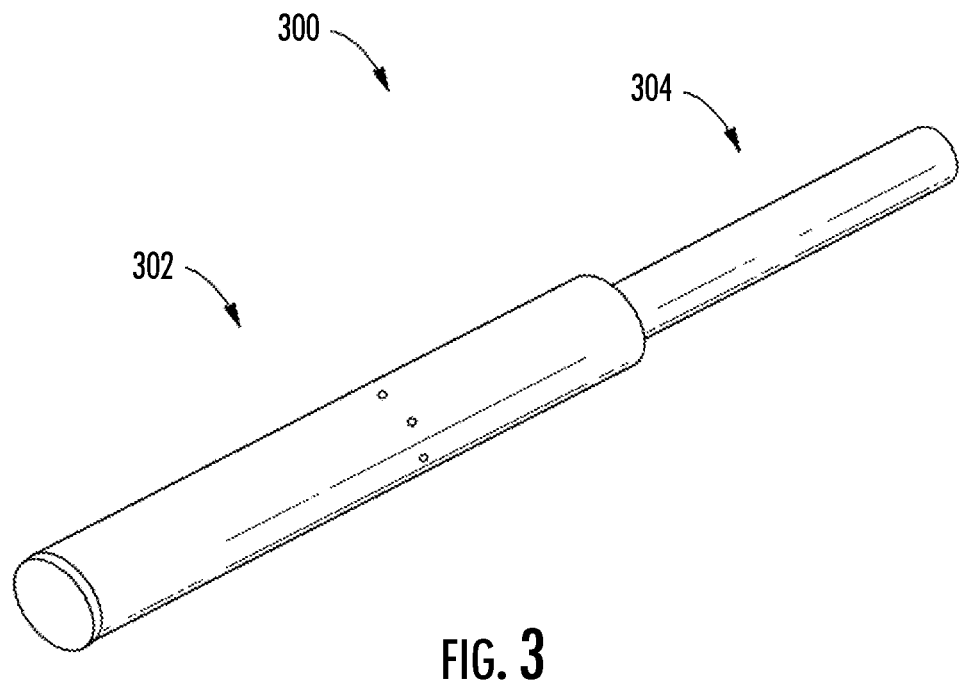
Figure 4:
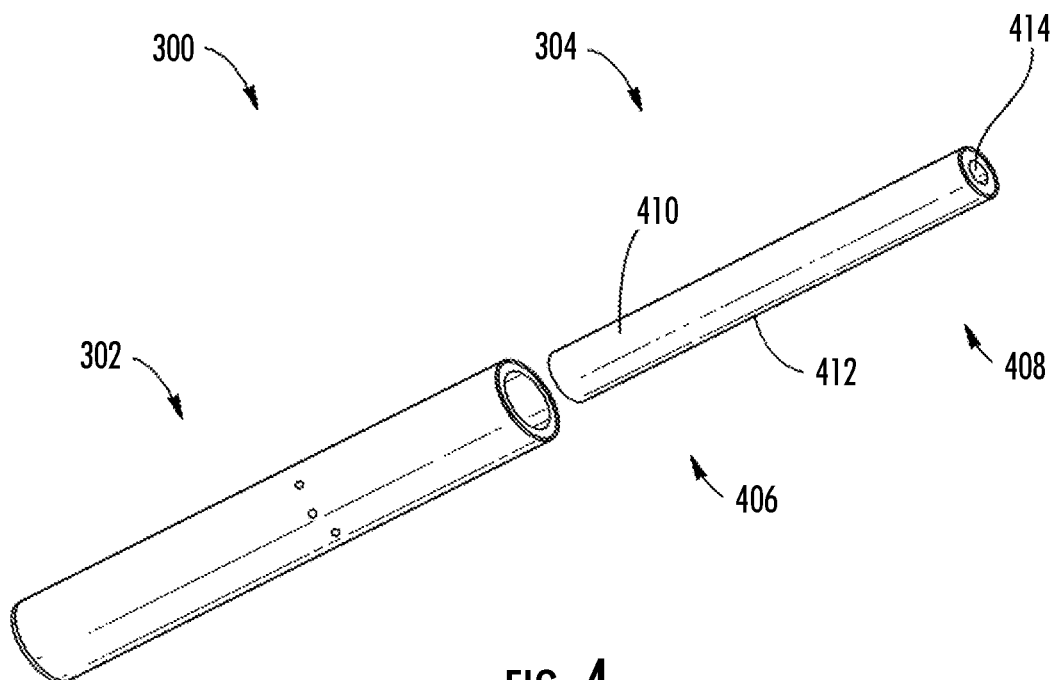
Figure 5:
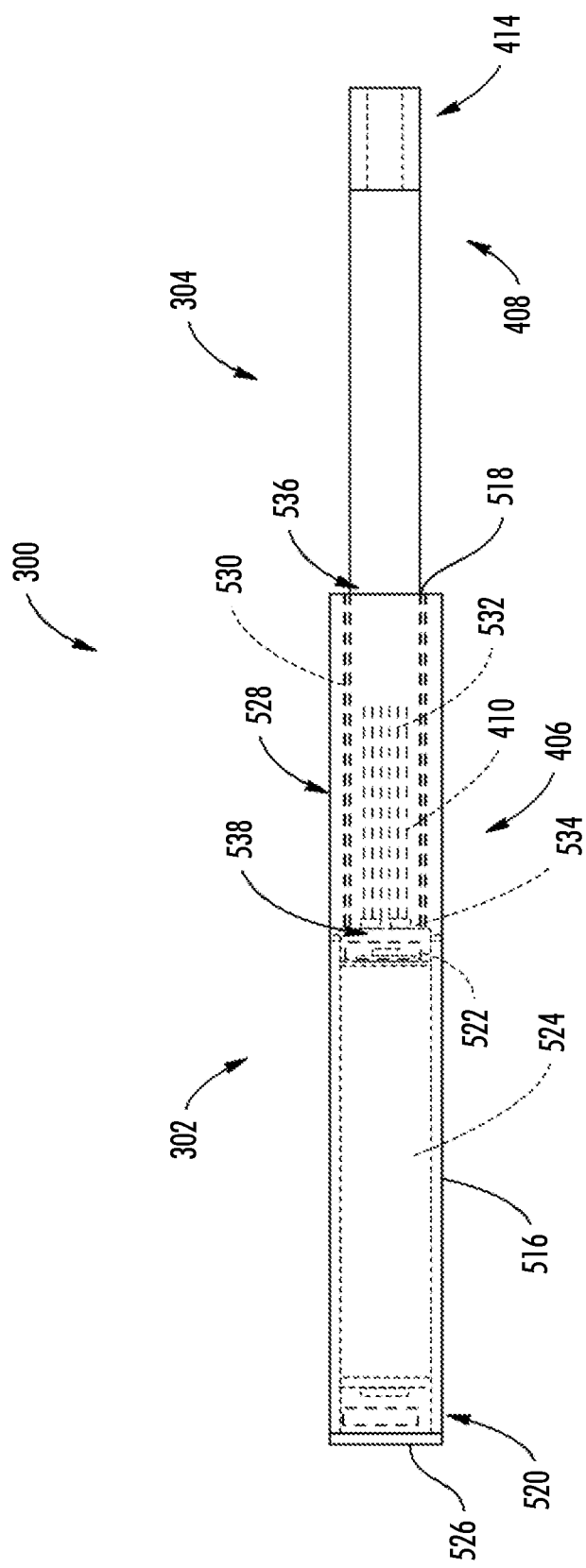
Figure 6:
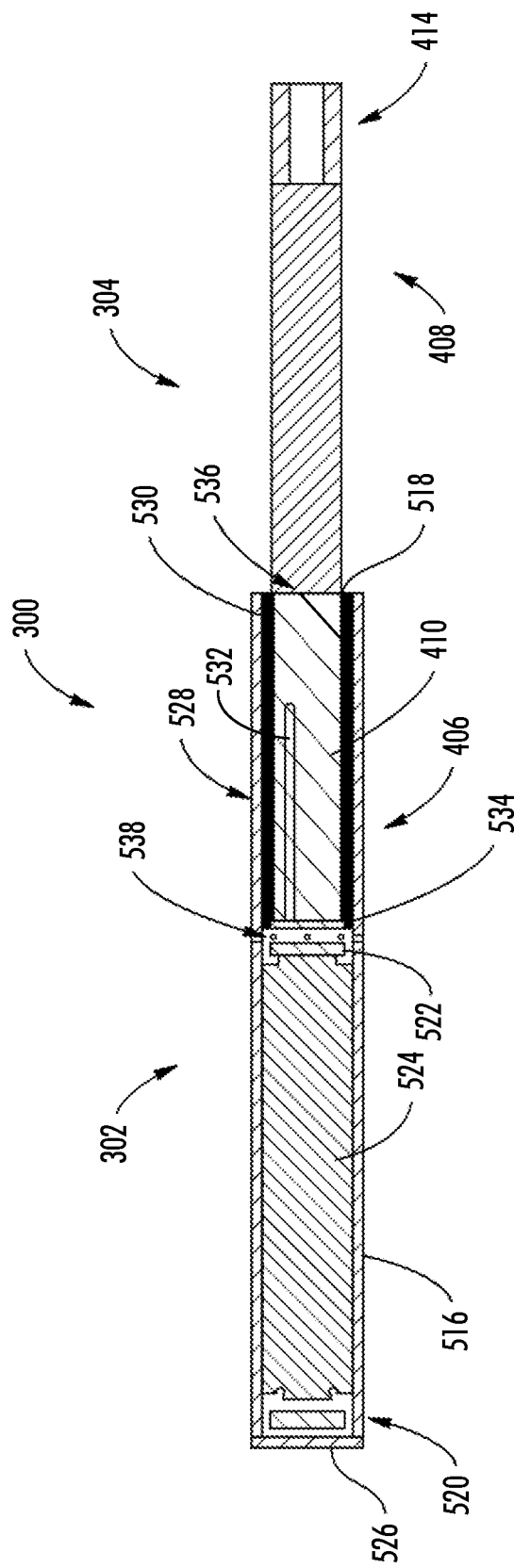
Figure 7:
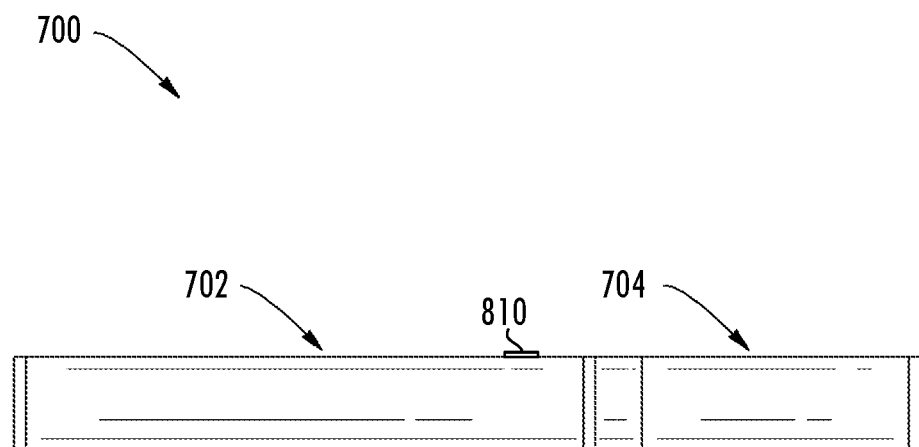
Figure 8:
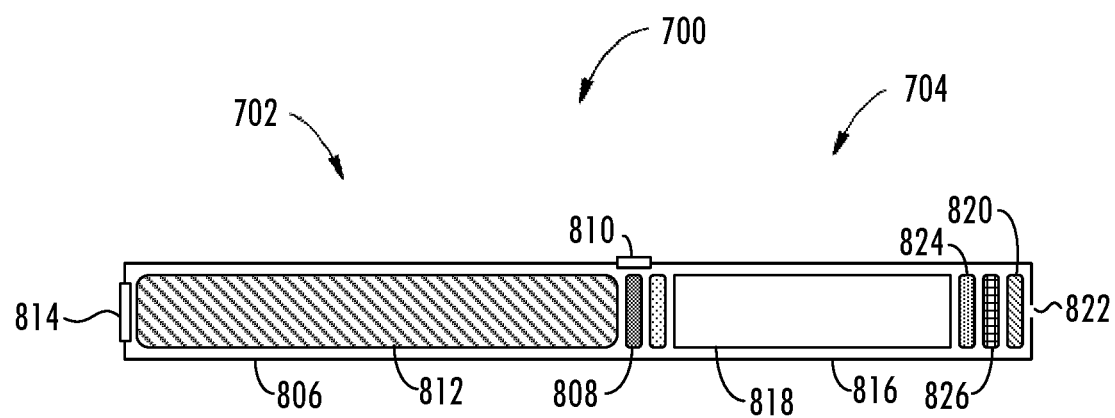
Figure 9:
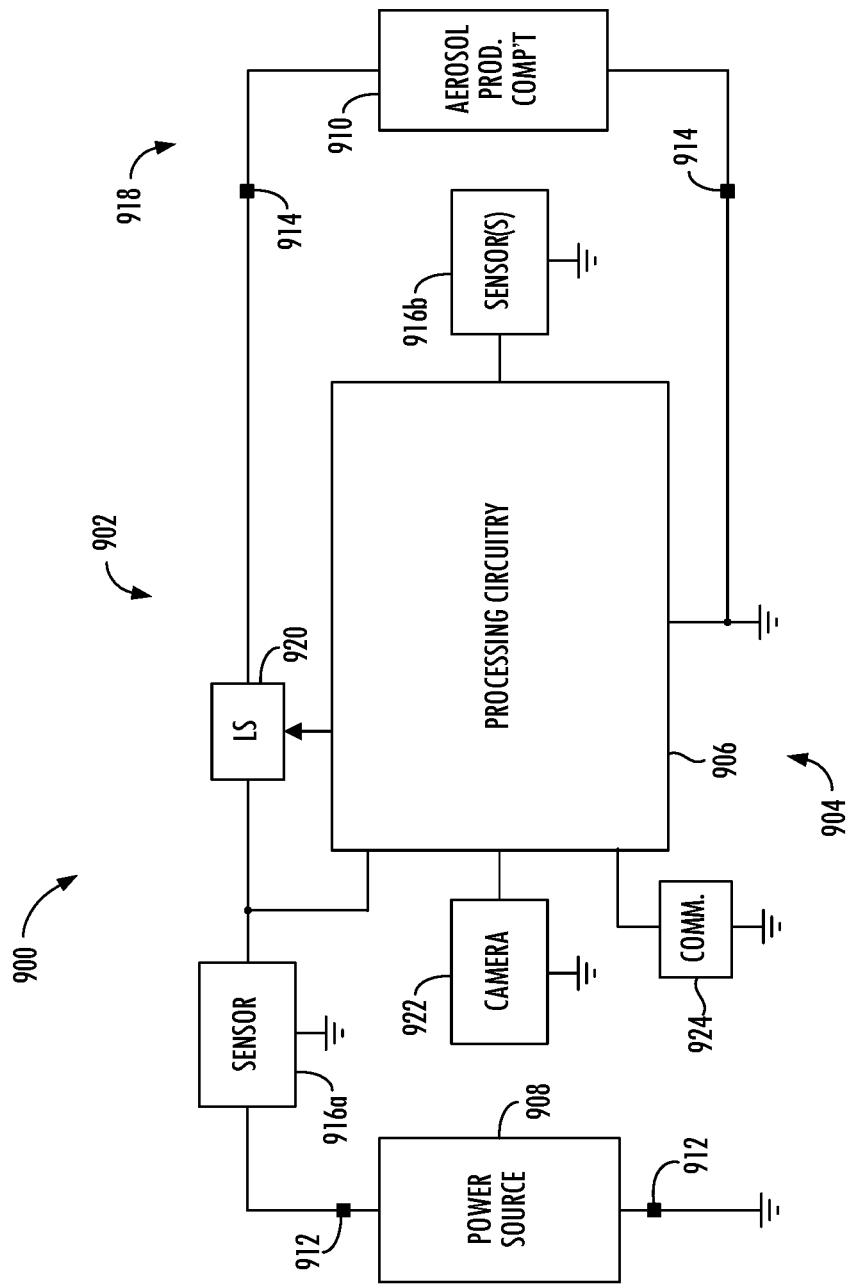

Having thus described aspects of the disclosure in the foregoing general terms, reference will now be made to the accompanying figures, which are not necessarily drawn to scale, and wherein:

FIG. 1 illustrates a perspective view of an aerosol delivery device including a cartridge and a control body that are coupled to one another, according to an example implementation of the present disclosure;

FIG. 2 is a partially cut-away view of the aerosol delivery device of FIG. 1 in which the cartridge and control body are decoupled from one another, according to an example implementation;

FIGS. 3 and 4 illustrate a perspective view of an aerosol delivery device comprising a control body and an aerosol source member that are respectively coupled to one another and decoupled from one another, according to another example implementation of the present disclosure;

FIGS. 5 and 6 illustrate respectively a front view of and a sectional view through the aerosol delivery device of FIGS. 3 and 4, according to an example implementation;

FIGS. 7 and 8 illustrate respectively a side view and a partially cut-away view of an aerosol delivery device including a cartridge coupled to a control body, according to example implementations;

FIG. 9 illustrates a circuit diagram of an aerosol delivery device according to various example implementations of the present disclosure; and FIG. 10 illustrates a communications system including an aerosol delivery device, according to various example implementations.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, the present disclosure relates to aerosol delivery devices. Aerosol delivery devices may be configured to produce an aerosol (an inhalable substance) from an aerosol precursor composition (sometimes referred to as an inhalable substance medium). The aerosol precursor composition may comprise one or more of a solid tobacco material, a semi-solid tobacco material, or a liquid aerosol precursor composition. In some implementations, the aerosol delivery devices may be configured to heat and produce an aerosol from a fluid aerosol precursor composition (e.g., a liquid aerosol precursor composition). Such aerosol delivery devices may include so-called electronic cigarettes. In other implementations, the aerosol delivery devices may comprise heat-not-burn devices. In yet other implementations, the aerosol delivery devices may comprise no-heat-no-burn devices.

Liquid aerosol precursor composition, also referred to as a vapor precursor composition or "e-liquid," is particularly useful for electronic cigarettes and no-heat-no-burn devices. Liquid aerosol precursor composition may comprise a variety of components including, by way of example, a polyhydric alcohol (e.g., glycerin (including vegetable glycerin), propylene glycol, or a mixture thereof), nicotine, tobacco, tobacco extract, and/or flavorants. In some examples, the aerosol precursor composition comprises glycerin and nicotine.

Some liquid aerosol precursor compositions that may be used in conjunction with various implementations may include one or more acids such as levulinic acid, succinic acid, lactic acid, pyruvic acid, benzoic acid, fumaric acid, combinations thereof, and the like. Inclusion of an acid(s) in liquid aerosol precursor compositions including nicotine may provide a protonated liquid aerosol precursor composition, including nicotine in salt form. Representative types of liquid aerosol precursor components and formulations are set forth and characterized in U.S. Pat. No. 7,726,320 to Robinson et al.; U.S. Pat. No. 9,254,002 to Chong et al.; and U.S. Pat. App. Pub. Nos. 2013/0008457 to Zheng et al., 2015/0020823 to Lipowicz et al., and 2015/0020830 to Koller; as well as PCT Pat. App. Pub. No. WO 2014/182736 to Bowen et al.; and U.S. Pat. No. 8,881,737 to Collett et al., the disclosures of which are incorporated herein by reference. Other aerosol precursors that may be employed include the aerosol precursors that have been incorporated in any of a number of the representative products identified above. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN. Implementations of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al.; U.S. Pat. No. 8,627,828 to Strickland et al.; and U.S. Pat. No. 9,307,787 to Sun et al.; as well as U.S. Pat. App. Pub. Nos. 2010/0018539 to Brinkley et al., and PCT Pat. App. Pub. No. WO 97/06786 to Johnson et al., all of which are incorporated by reference herein.

Representative types of substrates, reservoirs or other components for supporting the aerosol precursor are described in U.S. Pat. No. 8,528,569 to Newton; U.S. Pat. App. Pub. No. 2014/0261487 to Chapman et al.; U.S. Pat. App. Pub. No. 2015/0059780 to Davis et al.; and U.S. Pat. App. Pub. No. 2015/0216232 to Bless et al., all of which are incorporated herein by reference. Additionally, various wicking materials, and the configuration and operation of those wicking materials within certain types of electronic cigarettes, are set forth in U.S. Pat. No. 8,910,640 to Sears et al., which is incorporated herein by reference.

In other implementations, the aerosol delivery devices may comprise heat-not-burn devices, configured to heat a solid aerosol precursor composition (e.g., an extruded tobacco rod) or a semi-solid aerosol precursor composition (e.g., a glycerin-loaded tobacco paste). The aerosol precursor composition may comprise tobacco-containing beads, tobacco shreds, tobacco strips, reconstituted tobacco material, or combinations thereof, and/or a mix of finely ground tobacco, tobacco extract, spray dried tobacco extract, or other tobacco form mixed with optional inorganic materials (such as calcium carbonate), optional flavors, and aerosol forming materials to form a substantially solid or moldable (e.g., extrudable) substrate. Representative types of solid and semi-solid aerosol precursor compositions and formulations are disclosed in U.S. Pat. No. 8,424,538 to Thomas et al.; U.S. Pat. No. 8,464,726 to Sebastian et al.; U.S. Pat. App. Pub. No. 2015/0083150 to Conner et al.; U.S. Pat. App. Pub. No. 2015/0157052 to Ademe et al.; and U.S. Pat. App. Pub. No. 2017/0000188 to Nordskog et al., all of which are incorporated by reference herein. Further representative types of solid and semi-solid aerosol precursor compositions and arrangements include those found in the NEOSTIKS™ consumable aerosol source members for the GLO™ product by British American Tobacco and in the HEETS™ consumable aerosol source members for the IQOS™ product by Philip Morris International, Inc.

In various implementations, the inhalable substance specifically may be a tobacco component or a tobacco-derived material (i.e., a material that is found naturally in tobacco that may be isolated directly from the tobacco or synthetically prepared). For example, the aerosol precursor composition may comprise tobacco extracts or fractions thereof combined with an inert substrate. The aerosol precursor composition may further comprise unburned tobacco or a composition containing unburned tobacco that, when heated to a temperature below its combustion temperature, releases an inhalable substance. In some implementations, the aerosol precursor composition may comprise tobacco condensates or fractions thereof (i.e., condensed components of the smoke produced by the combustion of tobacco, leaving flavors and, possibly, nicotine).

Tobacco materials useful in the present disclosure can vary and may include, for example, flue-cured tobacco, burley tobacco, Oriental tobacco or Maryland tobacco, dark tobacco, dark-fired tobacco and *Rustica* tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), preferably in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al., U.S. Pat. No. 4,924,888 to Perfetti et al., U.S. Pat. No. 5,056,537 to Brown et al., U.S. Pat. No. 5,159,942 to Brinkley et al., U.S. Pat. No. 5,220,930 to Gentry, U.S. Pat. No. 5,360,023 to Blakley et al., U.S. Pat. No. 6,701,936 to Shafer et al., U.S. Pat. No. 7,011,096 to Li et al., U.S. Pat. No. 7,017,585 to Li et al., and U.S. Pat. No. 7,025,066 to Lawson et al.; U.S. Pat. App. Pub. No. 2004/0255965 to Perfetti et al.; PCT Pat. App. Pub. No. WO 02/37990 to Bereman; and Bombick et al., Fund. Appl. Toxicol., 39, p. 11-17 (1997), which are incorporated herein by reference. Further example tobacco compositions that may be useful in a smoking device, including according to the present disclosure, are disclosed in U.S. Pat. No. 7,726,320 to Robinson et al., which is incorporated herein by reference.

Still further, the aerosol precursor composition may comprise an inert substrate having the inhalable substance, or a precursor thereof, integrated therein or otherwise deposited thereon. For example, a liquid comprising the inhalable substance may be coated on or absorbed or adsorbed into the inert substrate such that, upon application of heat, the inhalable substance is released in a form that can be withdrawn from the inventive article through application of positive or negative pressure. In some aspects, the aerosol precursor composition may comprise a blend of flavorful and aromatic tobaccos in cut filler form. In another aspect, the aerosol precursor composition may comprise a reconstituted tobacco material, such as described in U.S. Pat. No. 4,807,809 to Pryor et al.; U.S. Pat. No. 4,889,143 to Pryor et al.; and U.S. Pat. No. 5,025,814 to Raker, the disclosures of which are incorporated herein by reference. For further information regarding suitable aerosol precursor composition, see U.S. patent application Ser. No. 15/916,834 to Sur et al., filed Mar. 9, 2018, which is incorporated herein by reference.

Regardless of the type of aerosol precursor composition, aerosol delivery devices may include an aerosol production component configured to produce an aerosol from the aerosol precursor composition. In the case of an electronic cigarette or a heat-not-burn device, for example, the aerosol production component may be or include a heating element. In the case of a no-heat-no-burn device, in some examples, the aerosol production component may be or include at least one vibratable piezoelectric or piezomagnetic mesh.

One example of a suitable heating element is an induction heater. Such heaters often comprise an induction transmitter and an induction receiver. The induction transmitter may include a coil configured to create an oscillating magnetic field (e.g., a magnetic field that varies periodically with time) when alternating current is directed through it. The induction receiver may be at least partially located or received within the induction transmitter and may include a conductive material (e.g., ferromagnetic material or an aluminum coated material). By directing alternating current through the induction transmitter, eddy currents may be generated in the induction receiver via induction. The eddy currents flowing through the resistance of the material defining the induction receiver may heat it by Joule heating (i.e., through the Joule effect). The induction receiver, which may define an atomizer, may be wirelessly heated to form an aerosol from an aerosol precursor composition positioned in proximity to the induction receiver. Various implementations of an aerosol delivery device with an induction heater are described in U.S. Pat. App. Pub. No. 2017/0127722 to Davis et al.; U.S. Pat. App. Pub. No. 2017/0202266 to Sur et al.; U.S. patent application Ser. No. 15/352,153 to Sur et al., filed Nov. 15, 2016; U.S. patent application Ser. No. 15/799,365 to Sebastian et al., filed Oct. 31, 2017; and U.S. patent application Ser. No. 15/836,086 to Sur, all of which are incorporated by reference herein.

In other implementations including those described more particularly herein, the heating element is a conductive heater such as in the case of electrical resistance heater. These heaters may be configured to produce heat when an electrical current is directed through it. In various implementations, a conductive heater may be provided in a variety forms, such as in the form of a foil, a foam, discs, spirals, fibers, wires, films, yarns, strips, ribbons or cylinders. Such heaters often include a metal material and are configured to produce heat as a result of the electrical resistance associated with passing an electrical current through it. Such resistive heaters may be positioned in proximity to and heat an aerosol precursor composition to produce an aerosol. A variety of conductive substrates that may be usable with the present disclosure are described in the above-cited U.S. Pat. App. Pub. No. 2013/0255702 to Griffith et al.

In some implementations aerosol delivery devices may include a control body and a cartridge in the case of so-called electronic cigarettes or no-heat-no-burn devices, or a control body and an aerosol source member in the case of heat-not-burn devices. In the case of either electronic cigarettes or heat-not-burn devices, the control body may be reusable, whereas the cartridge/aerosol source member may be configured for a limited number of uses and/or configured to be disposable. Various mechanisms may connect the cartridge/aerosol source member to the control body to result in a threaded engagement, a press-fit engagement, an interference fit, a sliding fit, a magnetic engagement, or the like.

The control body and cartridge/aerosol source member may include separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic, ceramics and the like.

The cartridge/aerosol source member may include the aerosol precursor composition. In order to produce aerosol from the aerosol precursor composition, the aerosol production component (e.g., heating element, piezoelectric/piezomagnetic mesh) may be positioned in contact with or proximate the aerosol precursor composition, such as across the control body and cartridge, or in the control body in which the aerosol source member may be positioned. The control body may include a power source, which may be rechargeable or replaceable, and thereby the control body may be reused with multiple cartridges/aerosol source members.

The control body may also include means to activate the aerosol delivery device such as a pushbutton, touch-sensitive surface or the like for manual control of the device. Additionally or alternatively, the control body may include a flow sensor to detect when a user draws on the cartridge/aerosol source member to thereby activate the aerosol delivery device.

In various implementations, the aerosol delivery device according to the present disclosure may have a variety of overall shapes, including, but not limited to an overall shape that may be defined as being substantially rod-like or substantially tubular shaped or substantially cylindrically shaped. In the implementations shown in and described with reference to the accompanying figures, the aerosol delivery device has a substantially round cross-section; however, other cross-sectional shapes (e.g., oval, square, rectangle, triangle, etc.) also are encompassed by the present disclosure. Such language that is descriptive of the physical shape of the article may also be applied to the individual components thereof, including the control body and the cartridge/aerosol source member. In other implementations, the control body may take another handheld shape, such as a small box shape.

In more specific implementations, one or both of the control body and the cartridge/aerosol source member may be referred to as being disposable or as being reusable. For example, the control body may have a power source such as a replaceable battery or a rechargeable battery, SSB, thin-film SSB, rechargeable supercapacitor, lithium-ion or hybrid lithium-ion supercapacitor, or the like. One example of a power source is a TKI-1550 rechargeable lithium-ion battery produced by Tadiran Batteries GmbH of Germany. In another implementation, a useful power source may be a N50-AAA CADNICA nickel-cadmium cell produced by Sanyo Electric Company, Ltd., of Japan. In other implementations, a plurality of such batteries, for example providing 1.2-volts each, may be connected in series.

In some examples, then, the power source may be connected to and thereby combined with any type of recharging technology. Examples of suitable chargers include chargers that simply supply constant or pulsed direct current (DC) power to the power source, fast chargers that add control circuitry, three-stage chargers, induction-powered chargers, smart chargers, motion-powered chargers, pulsed chargers, solar chargers, USB-based chargers and the like. In some examples, the charger includes a power adapter and any suitable charge circuitry. In other examples, the charger includes the power adapter and the control body is equipped with charge circuitry. In these other examples, the charger may at times be simply referred to as a power adapter.

The control body may include any of a number of different terminals, electrical connectors or the like to connect to a suitable charger, and in some examples, to connect to other peripherals for communication. More specific suitable examples include direct current (DC) connectors such as cylindrical connectors, cigarette lighter connectors and USB connectors including those specified by USB 1.x (e.g., Type A, Type B), USB 2.0 and its updates and additions (e.g., Mini A, Mini B, Mini AB, Micro A, Micro B, Micro AB) and USB 3.x (e.g., Type A, Type B, Micro B, Micro AB, Type C), proprietary connectors such as Apple's Lightning connector, and the like. The control body may directly connect with the charger or other peripheral, or the two may connect via an appropriate cable that also has suitable connectors. In examples in which the two are connected by cable, the control body and charger or other peripheral may have the same or different type of connector with the cable having the one type of connector or both types of connectors.

In examples involving induction-powered charging, the aerosol delivery device may be equipped with inductive wireless charging technology and include an induction receiver to connect with a wireless charger, charging pad or the like that includes an induction transmitter and uses inductive wireless charging (including for example, wireless charging according to the Qi wireless charging standard from the Wireless Power Consortium (WPC)). Or the power source may be recharged from a wireless radio frequency (RF) based charger. An example of an inductive wireless charging system is described in U.S. Pat. App. Pub. No. 2017/0112196 to Sur et al., which is incorporated herein by reference in its entirety. Further, in some implementations in the case of an electronic cigarette, the cartridge may comprise a single-use cartridge, as disclosed in U.S. Pat. No. 8,910,639 to Chang et al., which is incorporated herein by reference.

One or more connections may be employed to connect the power source to a recharging technology, and some may involve a charging case, cradle, dock, sleeve or the like. More specifically, for example, the control body may be configured to engage a cradle that includes a USB connector to connect to a power supply. Or in another example, the control body may be configured to fit within and engage a sleeve that includes a USB connector to connect to a power supply. In these and similar examples, the USB connector may connect directly to the power source, or the USB connector may connect to the power source via a suitable power adapter.

Examples of power sources are described in U.S. Pat. No. 9,484,155 to Peckerar et al.; and U.S. Pat. App. Pub. No. 2017/0112191 to Sur et al., filed Oct. 21, 2015, the disclosures of which are incorporated herein by reference. Other examples of a suitable power source are provided in U.S. Pat. App. Pub. No. 2014/0283855 to Hawes et al., U.S. Pat. App. Pub. No. 2014/0014125 to Fernando et al., U.S. Pat. App. Pub. No. 2013/0243410 to Nichols et al., U.S. Pat. App. Pub. No. 2010/0313901 to Fernando et al., and U.S. Pat. No. 9,439,454 to Fernando et al., all of which are incorporated herein by reference. With respect to the flow sensor, representative current regulating components and other current controlling components including various microcontrollers, sensors, and switches for aerosol delivery devices are described in U.S. Pat. No. 4,735,217 to Gerth et al.; U.S. Pat. Nos. 4,922,901, 4,947,874, and 4,947,875, all to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al.; U.S. Pat. No. 8,205,622 to Pan; U.S. Pat. No. 8,881,737 to Collet et al.; U.S. Pat. No. 9,423,152 to Ampolini et al.; U.S. Pat. No. 9,439,454 to Fernando et al.; and U.S. Pat. App. Pub. No. 2015/0257445 to Henry et al., all of which are incorporated herein by reference.

An input device may be included with the aerosol delivery device (and may replace or supplement a flow sensor). The input may be included to allow a user to control functions of the device and/or for output of information to a user. Any component or combination of components may be utilized as an input for controlling the function of the device. Suitable input devices include pushbuttons, touch switches or other touch sensitive surfaces. For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference.

As a further example, components adapted for gesture recognition based on specified movements of the aerosol delivery device may be used as an input device. See U.S. Pub. 2016/0158782 to Henry et al., which is incorporated herein by reference. As still a further example, a capacitive sensor may be implemented on the aerosol delivery device to enable a user to provide input, such as by touching a surface of the device on which the capacitive sensor is implemented. In another example, a sensor capable of detecting a motion associated with the device (e.g., accelerometer, gyroscope, photoelectric proximity sensor, etc.) may be implemented on the aerosol delivery device to enable a user to provide input. Examples of suitable sensors are described in U.S. Pat. App. Pub. No. 2018/0132528 to Sur et al.; and U.S. Pat. App. Pub. No. 2016/0158782 to Henry et al., which are incorporated herein by reference.

As indicated above, the aerosol delivery device may include various electronics such as at least one control component. A suitable control component may include a number of electronic components, and in some examples may be formed of a circuit board such as a printed circuit board (PCB). In some examples, the electronic components include processing circuitry configured to perform data processing, application execution, or other processing, control or management services according to one or more example implementations. The processing circuitry may include a processor embodied in a variety of forms such as at least one processor core, microprocessor, coprocessor, controller, microcontroller or various other computing or processing devices including one or more integrated circuits such as, for example, an ASIC (application specific integrated circuit), an FPGA (field programmable gate array), some combination thereof, or the like. In some examples, the processing circuitry may include memory coupled to or integrated with the processor, and which may store data, computer program instructions executable by the processor, some combination thereof, or the like.

In some examples, the control component may include one or more input/output peripherals, which may be coupled to or integrated with the processing circuitry. More particularly, the control component may include a communication interface to enable wireless communication with one or more networks, computing devices or other appropriately-enabled devices. Examples of suitable communication interfaces are disclosed in U.S. Pat. App. Pub. No. 2016/0261020 to Marion et al., the content of which is incorporated herein by reference. Another example of a suitable communication interface is the CC3200 single chip wireless microcontroller unit (MCU) from Texas Instruments. And examples of suitable manners according to which the aerosol delivery device may be configured to wirelessly communicate are disclosed in U.S. Pat. App. Pub. No. 2016/0007651 to Ampolini et al.; and U.S. Pat. App. Pub. No. 2016/0219933 to Henry, Jr. et al., each of which is incorporated herein by reference.

Still further components can be utilized in the aerosol delivery device of the present disclosure. One example of a suitable component is an indicator such as light-emitting diodes (LEDs), quantum dot-based LEDs or the like, which may be illuminated with use of the aerosol delivery device. Examples of suitable LED components, and the configurations and uses thereof, are described in U.S. Pat. No. 5,154,192 to Sprinkel et al.; U.S. Pat. No. 8,499,766 to Newton; U.S. Pat. No. 8,539,959 to Scatterday; and U.S. Pat. No. 9,451,791 to Sears et al., all of which are incorporated herein by reference.

Other indices of operation are also encompassed by the present disclosure. For example, visual indicators of operation also include changes in light color or intensity to show progression of the smoking experience. Tactile (haptic) indicators of operation such as vibration motors, and sound (audio) indicators of operation such as speakers, are similarly encompassed by the disclosure. Moreover, combinations of such indicators of operation also are suitable to be used in a single smoking article. According to another aspect, the aerosol delivery device may include one or more indicators or indicia, such as, for example, a display configured to provide information corresponding to the operation of the smoking article such as, for example, the amount of power remaining in the power source, progression of the smoking experience, indication corresponding to activating an aerosol production component, and/or the like.

Yet other components are also contemplated. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference.

Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.;

U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference. Further, U.S. Pat. App. Pub. No. 2017/0099877 to Worm et al., discloses capsules that may be included in aerosol delivery devices and fob-shape configurations for aerosol delivery devices, and is incorporated herein by reference. A variety of the materials disclosed by the foregoing documents may be incorporated into the present devices in various implementations, and all of the foregoing disclosures are incorporated herein by reference.

Yet other features, controls or components that can be incorporated into aerosol delivery devices of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. No. 2005/0016550 to Katase; U.S. Pat. No. 8,689,804 to Fernando et al.; U.S. Pat. App. Pub. No. 2013/0192623 to Tucker et al.; U.S. Pat. No. 9,427,022 to Leven et al.; U.S. Pat. App. Pub. No. 2013/0180553 to Kim et al.; U.S. Pat. App. Pub. No. 2014/0000638 to Sebastian et al.; U.S. Pat. App. Pub. No. 2014/0261495 to Novak et al.; and U.S. Pat. No. 9,220,302 to DePiano et al., all of which are incorporated herein by reference.

FIGS. 1 and 2 illustrate implementations of an aerosol delivery device including a control body and a cartridge in the case of an electronic cigarette. In this regard, FIGS. 1 and 2 illustrate an aerosol delivery device 100 according to an example implementation of the present disclosure. As indicated, the aerosol delivery device may include a control body 102 and a cartridge 104. The control body and the cartridge can be permanently or detachably aligned in a functioning relationship. In this regard, FIG. 1 illustrates a perspective view of the aerosol delivery device in a coupled configuration, whereas FIG. 2 illustrates a partially cut-away side view of the aerosol delivery device in a decoupled configuration. The aerosol delivery device may, for example, be substantially rod-like, substantially tubular shaped, or substantially cylindrically shaped in some implementations when the control body and the cartridge are in an assembled configuration.

The control body 102 and the cartridge 104 can be configured to engage one another by a variety of connections, such as a press fit (or interference fit) connection, a threaded connection, a magnetic connection, or the like. As such, the control body may include a first engaging element (e.g., a coupler) that is adapted to engage a second engaging element (e.g., a connector) on the cartridge. The first engaging element and the second engaging element may be reversible. As an example, either of the first engaging element or the second engaging element may be a male thread, and the other may be a female thread. As a further example, either the first engaging element or the second engaging element may be a magnet, and the other may be a metal or a matching magnet. In particular implementations, engaging elements may be defined directly by existing components of the control body and the cartridge. For example, the housing of the control body may define a cavity at an end thereof that is configured to receive at least a portion of the cartridge (e.g., a storage tank or other shell-forming element of the cartridge). In particular, a storage tank of the cartridge may be at least partially received within the cavity of the control body while a mouthpiece of the cartridge remains exposed outside of the cavity of the control body. The cartridge may be retained within the cavity formed by the control body housing, such as by an interference fit (e.g., through use of detents and/or other features creating an interference engagement between an outer surface of the cartridge and an interior surface of a wall forming the control body cavity), by a magnetic engagement (e.g., though use of magnets and/or magnetic metals positioned within the cavity of the control body and positioned on the cartridge), or by other suitable techniques.

As seen in the cut-away view illustrated in FIG. 2, the control body 102 and cartridge 104 each include a number of respective components. The components illustrated in FIG. 2 are representative of the components that may be present in a control body and cartridge and are not intended to limit the scope of components that are encompassed by the present disclosure. As shown, for example, the control body can be formed of a housing 206 (sometimes referred to as a control body shell) that can include a control component 208 (e.g., processing circuitry, etc.), a flow sensor 210, a power source 212 (e.g., battery, supercapacitor), and an indicator 214 (e.g., LED, quantum dot-based LED), and such components can be variably aligned. The power source may be rechargeable, and the control body may include charging circuitry coupled to and configured to controllably charge the power source.

The cartridge 104 can be formed of a housing 216 (sometimes referred to as the cartridge shell) enclosing a reservoir 218 configured to retain the aerosol precursor composition, and including a heating element 220 (aerosol production component). In various configurations, this structure may be referred to as a tank; and accordingly, the terms "cartridge," "tank" and the like may be used interchangeably to refer to a shell or other housing enclosing a reservoir for aerosol precursor composition, and including a heating element.

As shown, in some examples, the reservoir 218 may be in fluid communication with a liquid transport element 222 adapted to wick or otherwise transport an aerosol precursor composition stored in the reservoir housing to the heating element 220. In some examples, a valve may be positioned between the reservoir and heating element, and configured to control an amount of aerosol precursor composition passed or delivered from the reservoir to the heating element.

Various examples of materials configured to produce heat when electrical current is applied therethrough may be employed to form the heating element 220. The heating element in these examples may be a resistive heating element such as a wire coil, micro heater or the like. Example materials from which the heating element may be formed include Kanthal (FeCrAl), nichrome, nickel, stainless steel, indium tin oxide, tungsten, molybdenum disilicide ($MoSi_2$), molybdenum silicide (MoSi), molybdenum disilicide doped with aluminum ($Mo(Si,Al)_2$), titanium, platinum, silver, palladium, alloys of silver and palladium, graphite and graphite-based materials (e.g., carbon-based foams and yarns), conductive inks, boron doped silica, and ceramics (e.g., positive or negative temperature coefficient ceramics). The heating element may be resistive heating element or a heating element configured to generate heat through induction. The heating element may be coated by heat conductive ceramics such as aluminum nitride, silicon carbide, beryllium oxide, alumina, silicon nitride, or their composites. Example implementations of heating elements useful in aerosol delivery devices according to the present disclosure are further described below, and can be incorporated into devices such as those described herein.

An opening 224 may be present in the housing 216 (e.g., at the mouth end) to allow for egress of formed aerosol from the cartridge 104.

The cartridge 104 also may include one or more electronic components 226, which may include an integrated circuit, a memory component (e.g., EEPROM, flash memory), a sensor, or the like. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that various electronic components including the control component and the flow sensor may be combined on a circuit board (e.g., PCB) that supports and electrically connects the electronic components. Further, the circuit board may be positioned horizontally relative the illustration of FIG. 1 in that the circuit board can be lengthwise parallel to the central axis of the control body. In some examples, the air flow sensor may comprise its own circuit board or other base element to which it can be attached. In some examples, a flexible circuit board may be utilized. A flexible circuit board may be configured into a variety of shapes, include substantially tubular shapes. In some examples, a flexible circuit board may be combined with, layered onto, or form part or all of a heater substrate.

The control body 102 and the cartridge 104 may include components adapted to facilitate a fluid engagement therebetween. As illustrated in FIG. 2, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the heating element 220 in the cartridge. Further, the housing 206 can include an air intake 236, which may be a notch in the housing where it connects to the coupler that allows for passage of ambient air around the coupler and into the housing where it then passes through the cavity 232 of the coupler and into the cartridge through the projection 234.

A coupler and a base useful according to the present disclosure are described in U.S. Pat. App. Pub. No. 2014/0261495 to Novak et al., which is incorporated herein by reference. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the housing 216, in this example. An aerosol precursor composition can be retained in the reservoir. Liquid components, for example, can be sorptively retained by the reservoir. The reservoir can be in fluid connection with the liquid transport element 222. The liquid transport element can transport the aerosol precursor composition stored in the reservoir via capillary action—or via a micro pump—to the heating element 220 that is in the form of a metal wire coil in this example. As such, the heating element is in a heating arrangement with the liquid transport element.

In some examples, a microfluidic chip may be embedded in the reservoir 218, and the amount and/or mass of aerosol precursor composition delivered from the reservoir may be controlled by a micro pump, such as one based on microelectromechanical systems (MEMS) technology. Other example implementations of reservoirs and transport elements useful in aerosol delivery devices according to the present disclosure are further described herein, and such reservoirs and/or transport elements can be incorporated into devices such as those described herein. In particular, specific combinations of heating members and transport elements as further described herein may be incorporated into devices such as those described herein.

In use, when a user draws on the aerosol delivery device 100, airflow is detected by the flow sensor 210, and the heating element 220 is activated to vaporize components of the aerosol precursor composition. Drawing upon the mouth end of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heating element and out the opening 224 in the mouth end of the aerosol delivery device.

For further detail regarding implementations of an aerosol delivery device including a control body and a cartridge in the case of an electronic cigarette, see the above-cited U.S. patent application Ser. No. 15/836,086 to Sur; and U.S. patent application Ser. No. 15/916,834 to Sur et al.; as well as U.S. patent application Ser. No. 15/916,696 to Sur, filed Mar. 9, 2018, which is also incorporated herein by reference.

FIGS. 3-6 illustrate implementations of an aerosol delivery device including a control body and an aerosol source member in the case of a heat-not-burn device. More specifically, FIG. 3 illustrates an aerosol delivery device 300 according to an example implementation of the present disclosure. The aerosol delivery device may include a control body 302 and an aerosol source member 304. In various implementations, the aerosol source member and the control body can be permanently or detachably aligned in a functioning relationship. In this regard, FIG. 3 illustrates the aerosol delivery device in a coupled configuration, whereas FIG. 4 illustrates the aerosol delivery device in a decoupled configuration.

As shown in FIG. 4, in various implementations of the present disclosure, the aerosol source member 304 may comprise a heated end 406, which is configured to be inserted into the control body 302, and a mouth end 408, upon which a user draws to create the aerosol. In various implementations, at least a portion of the heated end may include an aerosol precursor composition 410.

In various implementations, the aerosol source member 304, or a portion thereof, may be wrapped in an exterior overwrap material 412, which may be formed of any material useful for providing additional structure and/or support for the aerosol source member. In various implementations, the exterior overwrap material may comprise a material that resists transfer of heat, which may include a paper or other fibrous material, such as a cellulose material. The exterior overwrap material may also include at least one filler material imbedded or dispersed within the fibrous material. In various implementations, the filler material may have the form of water insoluble particles. Additionally, the filler material may incorporate inorganic components. In various implementations, the exterior overwrap may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. The exterior overwrap may also include a material typically used in a filter element of a conventional cigarette, such as cellulose acetate. Further, an excess length of the overwrap at the mouth end 408 of the aerosol source member may function to simply separate the aerosol precursor composition 410 from the mouth of a consumer or to provide space for positioning of a filter material, as described below, or to affect draw on the article or to affect flow characteristics of the vapor or aerosol leaving the device during draw. Further discussion relating to the configurations for overwrap materials that may be used with the present disclosure may be found in the above-cited U.S. Pat. No. 9,078,473 to Worm et al.

In various implementations other components may exist between the aerosol precursor composition 410 and the mouth end 408 of the aerosol source member 304, wherein the mouth end may include a filter 414, which may, for example, be made of a cellulose acetate or polypropylene material. The filter may additionally or alternatively contain strands of tobacco containing material, such as described in U.S. Pat. No. 5,025,814 to Raker et al., which is incorporated herein by reference in its entirety. In various implementations, the filter may increase the structural integrity of the mouth end of the aerosol source member, and/or provide filtering capacity, if desired, and/or provide resistance to draw. In some implementations one or any combination of the following may be positioned between the aerosol precursor composition and the mouth end: an air gap; phase change materials for cooling air; flavor releasing media; ion exchange fibers capable of selective chemical adsorption; aerogel particles as filter medium; and other suitable materials.

Various implementations of the present disclosure employ one or more conductive heating elements to heat the aerosol precursor composition 410 of the aerosol source member 304. In various implementations, the heating element may be provided in a variety forms, such as in the form of a foil, a foam, a mesh, a hollow ball, a half ball, discs, spirals, fibers, wires, films, yarns, strips, ribbons, or cylinders. Such heating elements often comprise a metal material and are configured to produce heat as a result of the electrical resistance associated with passing an electrical current therethrough. Such resistive heating elements may be positioned in direct contact with, or in proximity to, the aerosol source member and particularly, the aerosol precursor composition of the aerosol source member. The heating element may be located in the control body and/or the aerosol source member. In various implementations, the aerosol precursor composition may include components (i.e., heat conducting constituents) that are imbedded in, or otherwise part of, the substrate portion that may serve as, or facilitate the function of, the heating assembly. Some examples of various heating members and elements are described in U.S. Pat. No. 9,078,473 to Worm et al.

Some non-limiting examples of various heating element configurations include configurations in which a heating element is placed in proximity with the aerosol source member 304. For instance, in some examples, at least a portion of a heating element may surround at least a portion of an aerosol source member. In other examples, one or more heating elements may be positioned adjacent an exterior of an aerosol source member when inserted in the control body 302. In other examples, at least a portion of a heating element may penetrate at least a portion of an aerosol source member (such as, for example, one or more prongs and/or spikes that penetrate an aerosol source member), when the aerosol source member is inserted into the control body. In some instances, the aerosol precursor composition may include a structure in contact with, or a plurality of beads or particles imbedded in, or otherwise part of, the aerosol precursor composition that may serve as, or facilitate the function of the heating element.

FIG. 5 illustrates a front view of an aerosol delivery device 300 according to an example implementation of the present disclosure, and FIG. 6 illustrates a sectional view through the aerosol delivery device of FIG. 5. In particular, the control body 302 of the depicted implementation may comprise a housing 516 that includes an opening 518 defined in an engaging end thereof, a flow sensor 520 (e.g., a puff sensor or pressure switch), a control component 522 (e.g., processing circuitry, etc.), a power source 524 (e.g., battery, supercapacitor), and an end cap that includes an indicator 526 (e.g., a LED). The power source may be rechargeable, and the control body may include charging circuitry coupled to and configured to controllably charge the power source.

In one implementation, the indicator 526 may comprise one or more LEDs, quantum dot-based LEDs or the like. The indicator can be in communication with the control component 522 and be illuminated, for example, when a user draws on the aerosol source member 304, when coupled to the control body 302, as detected by the flow sensor 520.

The control body 302 of the depicted implementation includes one or more heating assemblies 528 (individually or collectively referred to a heating assembly) configured to heat the aerosol precursor composition 410 of the aerosol source member 304. Although the heating assembly of various implementations of the present disclosure may take a variety of forms, in the particular implementation depicted in FIGS. 5 and 6, the heating assembly comprises an outer cylinder 530 and a heating element 532 (aerosol production component), which in this implementation comprises a plurality of heater prongs that extend from a receiving base 534 (in various configurations, the heating assembly or more specifically the heater prongs may be referred to as a heater). In the depicted implementation, the outer cylinder comprises a double-walled vacuum tube constructed of stainless steel so as to maintain heat generated by the heater prongs within the outer cylinder, and more particularly, maintain heat generated by heater prongs within the aerosol precursor composition. In various implementations, the heater prongs may be constructed of one or more conductive materials, including, but not limited to, copper, aluminum, platinum, gold, silver, iron, steel, brass, bronze, graphite, or any combination thereof.

As illustrated, the heating assembly 528 may extend proximate an engagement end of the housing 516, and may be configured to substantially surround a portion of the heated end 406 of the aerosol source member 304 that includes the aerosol precursor composition 410. In such a manner, the heating assembly may define a generally tubular configuration. As illustrated in FIGS. 5 and 6, the heating element 532 (e.g., plurality of heater prongs) is surrounded by the outer cylinder 530 to create a receiving chamber 536. In such a manner, in various implementations the outer cylinder may comprise a nonconductive insulating material and/or construction including, but not limited to, an insulating polymer (e.g., plastic or cellulose), glass, rubber, ceramic, porcelain, a double-walled vacuum structure, or any combinations thereof.

In some implementations, one or more portions or components of the heating assembly 528 may be combined with, packaged with, and/or integral with (e.g., embedded within) the aerosol precursor composition 410. For example, in some implementations the aerosol precursor composition may be formed of a material as described above and may include one or more conductive materials mixed therein. In some of these implementations, contacts may be connected directly to the aerosol precursor composition such that, when the aerosol source member is inserted into the receiving chamber of the control body, the contacts make electrical connection with the electrical energy source. Alternatively, the contacts may be integral with the electrical energy source and may extend into the receiving chamber such that, when the aerosol source member is inserted into the receiving chamber of the control body, the contacts make electrical connection with the aerosol precursor composition. Because of the presence of the conductive material in the aerosol precursor composition, the application of power from the electrical energy source to the aerosol precursor composition allows electrical current to flow and thus produce heat from the conductive material. Thus, in some implementations the heating element may be described as being integral with the aerosol precursor composition. As a non-limiting example, graphite or other suitable, conductive material may be mixed with, embedded in, or otherwise present directly on or within the material forming the aerosol precursor composition to make the heating element integral with the medium.

As noted above, in the illustrated implementation, the outer cylinder 530 may also serve to facilitate proper positioning of the aerosol source member 304 when the aerosol source member is inserted into the housing 516. In various implementations, the outer cylinder of the heating assembly 528 may engage an internal surface of the housing to provide for alignment of the heating assembly with respect to the housing. Thereby, as a result of the fixed coupling between the heating assembly, a longitudinal axis of the heating assembly may extend substantially parallel to a longitudinal axis of the housing. In particular, the support cylinder may extend from the opening 518 of the housing to the receiving base 534 to create the receiving chamber 536.

The heated end 406 of the aerosol source member 304 is sized and shaped for insertion into the control body 302. In various implementations, the receiving chamber 536 of the control body may be characterized as being defined by a wall with an inner surface and an outer surface, the inner surface defining the interior volume of the receiving chamber. For example, in the depicted implementations, the outer cylinder 530 defines an inner surface defining the interior volume of the receiving chamber. In the illustrated implementation, an inner diameter of the outer cylinder may be slightly larger than or approximately equal to an outer diameter of a corresponding aerosol source member (e.g., to create a sliding fit) such that the outer cylinder is configured to guide the aerosol source member into the proper position (e.g., lateral position) with respect to the control body. Thus, the largest outer diameter (or other dimension depending upon the specific cross-sectional shape of the implementations) of the aerosol source member may be sized to be less than the inner diameter (or other dimension) at the inner surface of the wall of the open end of the receiving chamber in the control body. In some implementations, the difference in the respective diameters may be sufficiently small so that the aerosol source member fits snugly into the receiving chamber, and frictional forces prevent the aerosol source member from being moved without an applied force. On the other hand, the difference may be sufficient to allow the aerosol source member to slide into or out of the receiving chamber without requiring undue force.

In the illustrated implementation, the control body 302 is configured such that when the aerosol source member 304 is inserted into the control body, the heating element 532 (e.g., heater prongs) is located in the approximate radial center of at least a portion of the aerosol precursor composition 410 of the heated end 406 of the aerosol source member. In such a manner, when used in conjunction with a solid or semi-solid aerosol precursor composition, the heater prongs may be in direct contact with the aerosol precursor composition. In other implementations, such as when used in conjunction with an extruded aerosol precursor composition that defines a tube structure, the heater prongs may be located inside of a cavity defined by an inner surface of the extruded tube structure, and would not contact the inner surface of the extruded tube structure.

During use, the consumer initiates heating of the heating assembly 528, and in particular, the heating element 532 that is adjacent the aerosol precursor composition 410 (or a specific layer thereof). Heating of the aerosol precursor composition releases the inhalable substance within the aerosol source member 304 so as to yield the inhalable substance. When the consumer inhales on the mouth end 408 of the aerosol source member, air is drawn into the aerosol source member through an air intake 538 such as openings or apertures in the control body 302. The combination of the drawn air and the released inhalable substance is inhaled by the consumer as the drawn materials exit the mouth end of the aerosol source member. In some implementations, to initiate heating, the consumer may manually actuate a pushbutton or similar component that causes the heating element of the heating assembly to receive electrical energy from the battery or other energy source. The electrical energy may be supplied for a pre-determined length of time or may be manually controlled.

In some implementations, flow of electrical energy does not substantially proceed in between puffs on the device 300 (although energy flow may proceed to maintain a baseline temperature greater than ambient temperature—e.g., a temperature that facilitates rapid heating to the active heating temperature). In the depicted implementation, however, heating is initiated by the puffing action of the consumer through use of one or more sensors, such as flow sensor 520. Once the puff is discontinued, heating will stop or be reduced. When the consumer has taken a sufficient number of puffs so as to have released a sufficient amount of the inhalable substance (e.g., an amount sufficient to equate to a typical smoking experience), the aerosol source member 304 may be removed from the control body 302 and discarded. In some implementations, further sensing elements, such as capacitive sensing elements and other sensors, may be used as discussed in U.S. patent application Ser. No. 15/707,461 to Phillips et al., which is incorporated herein by reference.

In various implementations, the aerosol source member 304 may be formed of any material suitable for forming and maintaining an appropriate conformation, such as a tubular shape, and for retaining therein the aerosol precursor composition 410. In some implementations, the aerosol source member may be formed of a single wall or, in other implementations, multiple walls, and may be formed of a material (natural or synthetic) that is heat resistant so as to retain its structural integrity—e.g., does not degrade—at least at a temperature that is the heating temperature provided by the electrical heating element, as further discussed herein. While in some implementations, a heat resistant polymer may be used, in other implementations, the aerosol source member may be formed from paper, such as a paper that is substantially straw-shaped. As further discussed herein, the aerosol source member may have one or more layers associated therewith that function to substantially prevent movement of vapor therethrough. In one example implementation, an aluminum foil layer may be laminated to one surface of the aerosol source member. Ceramic materials also may be used. In further implementations, an insulating material may be used so as not to unnecessarily move heat away from the aerosol precursor composition. Further example types of components and materials that may be used to provide the functions described above or be used as alternatives to the materials and components noted above can be those of the types set forth in U.S. Pat. App. Pub. Nos. 2010/00186757 to Crooks et al., 2010/00186757 to Crooks et al., and 2011/0041861 to Sebastian et al., all of which are incorporated herein by reference.

In the depicted implementation, the control body 302 includes a control component 522 that controls the various functions of the aerosol delivery device 300, including providing power to the electrical heating element 532. For example, the control component may include processing circuitry (which may be connected to further components, as further described herein) that is connected by electrically conductive wires (not shown) to the power source 524. In various implementations, the processing circuitry may control when and how the heating assembly 528, and particularly the heater prongs, receives electrical energy to heat the aerosol precursor composition 410 for release of the inhalable substance for inhalation by a consumer. In some implementations, such control may be activated by a flow sensor 520 as described in greater detail above.

As seen in FIGS. 5 and 6, the heating assembly 528 of the depicted implementation comprises an outer cylinder 530 and a heating element 532 (e.g., plurality of heater prongs) that extend from a receiving base 534. In some implementations, such as those wherein the aerosol precursor composition 410 comprises a tube structure, the heater prongs may be configured to extend into a cavity defined by the inner surface of the aerosol precursor composition. In other implementations, such as the depicted implementation wherein the aerosol precursor composition comprises a solid or semi-solid, the plurality of heater prongs are configured to penetrate into the aerosol precursor composition contained in the heated end 406 of the aerosol source member 304 when the aerosol source member is inserted into the control body 302. In such implementations, one or more of the components of the heating assembly, including the heater prongs and/or the receiving base, may be constructed of a non-stick or stick-resistant material, for example, certain aluminum, copper, stainless steel, carbon steel, and ceramic materials. In other implementations, one or more of the components of the heating assembly, including the heater prongs and/or the receiving base, may include a non-stick coating, including, for example, a polytetrafluoroethylene (PTFE) coating, such as Teflon®, or other coatings, such as a stick-resistant enamel coating, or a ceramic coating, such as Greblon®, or Thermolon™.

In addition, although in the depicted implementation there are multiple heater prongs 532 that are substantially equally distributed about the receiving base 534, it should be noted that in other implementations, any number of heater prongs may be used, including as few as one, with any other suitable spatial configuration. Furthermore, in various implementations the length of the heater prongs may vary. For example, in some implementations the heater prongs may comprise small projections, while in other implementations the heater prongs may extend any portion of the length of the receiving chamber 536, including up to about 25%, up to about 50%, up to about 75%, and up to about the full length of the receiving chamber. In still other implementations, the heating assembly 528 may take on other configurations. Examples of other heater configurations that may be adapted for use in the present invention per the discussion provided above can be found in U.S. Pat. No. 5,060,671 to Counts et al., U.S. Pat. No. 5,093,894 to Deevi et al., U.S. Pat. No. 5,224,498 to Deevi et al., U.S. Pat. No. 5,228,460 to Sprinkel Jr., et al., U.S. Pat. No. 5,322,075 to Deevi et al., U.S. Pat. No. 5,353,813 to Deevi et al., U.S. Pat. No. 5,468,936 to Deevi et al., U.S. Pat. No. 5,498,850 to Das, U.S. Pat. No. 5,659,656 to Das, U.S. Pat. No. 5,498,855 to Deevi et al., U.S. Pat. No. 5,530,225 to Hajaligol, U.S. Pat. No. 5,665,262 to Hajaligol, and U.S. Pat. No. 5,573,692 to Das et al.; and U.S. Pat. No. 5,591,368 to Fleischhauer et al., which are incorporated herein by reference.

In various implementations, the control body 302 may include an air intake 538 (e.g., one or more openings or apertures) therein for allowing entrance of ambient air into the interior of the receiving chamber 536. In such a manner, in some implementations the receiving base 534 may also include an air intake. Thus, in some implementations when a consumer draws on the mouth end of the aerosol source member 304, air can be drawn through the air intake of the control body and the receiving base into the receiving chamber, pass into the aerosol source member, and be drawn through the aerosol precursor composition 410 of the aerosol source member for inhalation by the consumer. In some implementations, the drawn air carries the inhalable substance through the optional filter 414 and out of an opening at the mouth end 408 of the aerosol source member. With the heating element 532 positioned inside the aerosol precursor composition, the heater prongs may be activated to heat the aerosol precursor composition and cause release of the inhalable substance through the aerosol source member.

As described above with reference to FIGS. 5 and 6 in particular, various implementations of the present disclosure employ a conductive heater to heat the aerosol precursor composition 410. As also indicated above, various other implementations employ an induction heater to heat the aerosol precursor composition. In some of these implementations, the heating assembly 528 may be configured as an induction heater that comprises a transformer with an induction transmitter and an induction receiver. In implementations in which the heating assembly is configured as the induction heater, the outer cylinder 530 may be configured as the induction transmitter, and the heating element 532 (e.g., plurality of heater prongs) that extend from the receiving base 534 may be configured as the induction receiver. In various implementations, one or both of the induction transmitter and induction receiver may be located in the control body 302 and/or the aerosol source member 304.

In various implementations, the outer cylinder 530 and heating element 532 as the induction transmitter and induction receiver may be constructed of one or more conductive materials, and in further implementations the induction receiver may be constructed of a ferromagnetic material including, but not limited to, cobalt, iron, nickel, and combinations thereof. In one example implementation, the foil material is constructed of a conductive material and the heater prongs are constructed of a ferromagnetic material. In various implementations, the receiving base may be constructed of a non-conductive and/or insulating material.

The outer cylinder 530 as the induction transmitter may include a laminate with a foil material that surrounds a support cylinder. In some implementations, the foil material may include an electrical trace printed thereon, such as, for example, one or more electrical traces that may, in some implementations, form a helical coil pattern when the foil material is positioned around the heating element 532 as the induction receiver. The foil material and support cylinder may each define a tubular configuration. The support cylinder may be configured to support the foil material such that the foil material does not move into contact with, and thereby short-circuit with, the heater prongs. In such a manner, the support cylinder may comprise a nonconductive material, which may be substantially transparent to an oscillating magnetic field produced by the foil material. In various implementations, the foil material may be imbedded in, or otherwise coupled to, the support cylinder. In the illustrated implementation, the foil material is engaged with an outer surface of the support cylinder; however, in other implementations, the foil material may be positioned at an inner surface of the support cylinder or be fully imbedded in the support cylinder.

The foil material of the outer cylinder 530 may be configured to create an oscillating magnetic field (e.g., a magnetic field that varies periodically with time) when alternating current is directed through it. The heater prongs of the heating element 532 may be at least partially located or received within the outer cylinder and include a conductive material. By directing alternating current through the foil material, eddy currents may be generated in the heater prongs via induction. The eddy currents flowing through the resistance of the material defining the heater prongs may heat it by Joule heating (i.e., through the Joule effect). The heater prongs may be wirelessly heated to form an aerosol from the aerosol precursor composition 410 positioned in proximity to the heater prongs.

Other implementations of the aerosol delivery device, control body and aerosol source member are described in the above-cited U.S. patent application Ser. No. 15/916,834 to Sur et al.; U.S. patent application Ser. No. 15/916,696 to Sur; and U.S. patent application Ser. No. 15/836,086 to Sur.

FIGS. 7 and 8 illustrate implementations of an aerosol delivery device including a control body and a cartridge in the case of a no-heat-no-burn device. In this regard, FIG. 7 illustrates a side view of an aerosol delivery device 700 including a control body 702 and a cartridge 704, according to various example implementations of the present disclosure. In particular, FIG. 7 illustrates the control body and the cartridge coupled to one another. The control body and the cartridge may be detachably aligned in a functioning relationship.

FIG. 8 more particularly illustrates the aerosol delivery device 700, in accordance with some example implementations. As seen in the cut-away view illustrated therein, again, the aerosol delivery device can comprise a control body 702 and a cartridge 704 each of which include a number of respective components. The components illustrated in FIG. 8 are representative of the components that may be present in a control body and cartridge and are not intended to limit the scope of components that are encompassed by the present disclosure. As shown, for example, the control body can be formed of a control body housing or shell 806 that can include a control component 808 (e.g., processing circuitry, etc.), an input device 810, a power source 812 and an indicator 814 (e.g., LED, quantum dot-based LED), and such components can be variably aligned. Here, a particular example of a suitable control component includes the PIC16 (L)F1713/6 microcontrollers from Microchip Technology Inc., which is described in Microchip Technology, Inc., AN2265, *Vibrating Mesh Nebulizer Reference Design* (2016), which is incorporated by reference.

The cartridge 704 can be formed of a housing—referred to at times as a cartridge shell 816—enclosing a reservoir 818 configured to retain the aerosol precursor composition, and including a nozzle 820 having at least one piezoelectric/piezomagnetic mesh (aerosol production component). Similar to above, in various configurations, this structure may be referred to as a tank; and accordingly, the terms "cartridge," "tank" and the like may be used interchangeably to refer to a shell or other housing enclosing a reservoir for aerosol precursor composition, and including a nozzle.

The reservoir 818 illustrated in FIG. 8 can be a container or can be a fibrous reservoir, as presently described. The reservoir may be in fluid communication with the nozzle 820 for transport of an aerosol precursor composition stored in the reservoir housing to the nozzle. An opening 822 may be present in the cartridge shell 816 (e.g., at the mouthend) to allow for egress of formed aerosol from the cartridge 704.

In some examples, a transport element may be positioned between the reservoir 818 and nozzle 820, and configured to control an amount of aerosol precursor composition passed or delivered from the reservoir to the nozzle. In some examples, a microfluidic chip may be embedded in the cartridge 704, and the amount and/or mass of aerosol precursor composition delivered from the reservoir may be controlled by one or more microfluidic components. One example of a microfluidic component is a micro pump 824, such as one based on microelectromechanical systems (MEMS) technology. Examples of suitable micro pumps include the model MDP2205 micro pump and others from thinXXS Microtechnology AG, the mp5 and mp6 model micro pumps and others from Bartels Mikrotechnik GmbH, and piezoelectric micro pumps from Takasago Fluidic Systems.

As also shown, in some examples, a micro filter 826 may be positioned between the micro pump 824 and nozzle 820 to filter aerosol precursor composition delivered to the nozzle. Like the micro pump, the micro filter is a microfluidic component. Examples of suitable micro filters include flow-through micro filters those manufactured using lab-on-a-chip (LOC) techniques.

In use, when the input device 810 detects user input to activate the aerosol delivery device, the piezoelectric/piezomagnetic mesh is activated to vibrate and thereby draw aerosol precursor composition through the mesh. This forms droplets of aerosol precursor composition that combine with air to form an aerosol. The aerosol is whisked, aspirated or otherwise drawn away from the mesh and out the opening 822 in the mouthend of the aerosol delivery device.

The aerosol delivery device 700 can incorporate the input device 810 such as a switch, sensor or detector for control of supply of electric power to the at least one piezoelectric/piezomagnetic mesh of the nozzle 820 when aerosol generation is desired (e.g., upon draw during use). As such, for example, there is provided a manner or method of turning off power to the mesh when the aerosol delivery device is not being drawn upon during use, and for turning on power to actuate or trigger the production and dispensing of aerosol from the nozzle during draw. Additional representative types of sensing or detection mechanisms, structure and configuration thereof, components thereof, and general methods of operation thereof, are described above and in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference.

For more information regarding the above and other implementations of an aerosol delivery device in the case of a no-heat-no-burn device, see U.S. patent application Ser. No. 15/651,548 to Sur, filed Jul. 17, 2017, which is incorporated herein by reference.

As described above, the aerosol delivery device of example implementations may include various electronic components in the context of an electronic cigarette, heat-not-burn device or no-heat-no-burn device, or even in the case of a device that includes the functionality of one or more of an electronic cigarette, heat-not-burn device or no-heat-no-burn device. FIG. 9 illustrates a circuit diagram of an aerosol delivery device 900 that may be or incorporate functionality of any one or more of aerosol delivery devices 100, 300, 700 according to various example implementations of the present disclosure.

As shown in FIG. 9, the aerosol delivery device 900 includes a control body 902 with a control component 904 (with processing circuitry 906) and a power source 908 that may correspond to or include functionality of respective ones of the control body 102, 302, 702, control component 208, 522, 808, and power source 212, 524, 812. The aerosol delivery device also includes an aerosol production component 910 that may correspond to or include functionality of heating element 222, 534, or piezoelectric/piezomagnetic mesh of nozzle 820. In some implementations, aerosol delivery device and in particular the control body includes terminals 912 configured to connect the power source 904 to the aerosol delivery device or in particular the control body. The control body may include the aerosol production component or second terminals 914 configured to connect the aerosol production component to the control body.

In some examples, the aerosol delivery device 900 includes at least one sensor 916, including in some examples a first sensor 916*a* and/or one or more second sensors 916*b*, configured to produce measurements of properties during use of the aerosol delivery device 900. In this regard, the first sensor may correspond to or include functionality of sensor 210, 520, or input device 810. The first sensor may be a pressure sensor configured to produce measurements of pressure caused by a flow of air through at least a portion of the aerosol delivery device, or otherwise receive input to indicate use of the aerosol delivery device. The first sensor is configured to convert the measurements/user input to corresponding electrical signals, which may include conversion of analog to digital. In some examples, this first sensor may be a digital sensor, digital pressure sensor or the like, some suitable examples of which are manufactured by Murata Manufacturing Co., Ltd.

The processing circuitry 906 may be configured to switchably connect the power source 908 to a load 918 including the aerosol production component 910 and thereby power the aerosol production component. More particularly, for example, the processing circuitry may be configured to receive the corresponding electrical signals from the first sensor 916*a*, and in response connect the power source to the load including the aerosol production component and thereby power the aerosol production component. The processing circuitry may be configured to process the corresponding electrical signals to determine an on/off condition, and may modulate switching connection of the power source to the load in proportion to the measurements/user input produced by the first sensor. In some examples, the control component 904 further includes a high-side load switch (LS) 920 between the first sensor and the load, and controllable by the processing circuitry to connect and disconnect the power source to and from the load including the aerosol production component.

The second sensor(s) 916*b*, like the first sensor 916*a*, are also configured to produce measurements of properties during use of the aerosol delivery device 900. These second sensor(s) may include any of a number of different types of sensors. Examples of suitable sensors include a current sensor, a voltage sensor, a resistance sensor, a machine-readable information reader, a position sensor, an accelerometer, a microphone and the like. The machine-readable information reader in particular is a reader configured to read machine-readable information, such as according to any of a number of different automatic identification and data capture (AIDC) techniques (e.g., barcode, radio-frequency identification, etc.). The position sensor is configured to determine its geographic position in a number of different manners, such as by interaction with a satellite navigation system like the Global Positioning System (GPS). In this regard, geographic position may be given in coordinates (e.g., latitude, longitude). In other examples, geographic position may be given by address or other identifier of a structure or plot of land, or even further by location within the structure or plot of land. In a particular example, geographic position may be given by the address of the user's workplace, or perhaps even more specifically the location of the smoking lounge in the user's workplace.

Although also a sensor, shown separately in FIG. 9, the aerosol delivery device 900 in some examples also includes a camera system with a digital camera 922 and supporting electronics, which in some examples may include the processing circuitry 906. The digital camera may be configured to capture images of an object or scene in its field of view, and these images may be transferrable locally onboard the aerosol delivery device or to an external computing device. The images may include still images or video, or in some examples, the digital camera may be configured to selectively capture still images or capture video. More information regarding a suitable camera system is described in U.S. Pat. No. 9,955,733 to Sur et al., which is incorporated herein by reference.

As described above, in some examples, the control component 904 includes a communication interface 924 to enable wireless communication with one or more networks, computing devices or other appropriately-enabled devices. In this regard, FIG. 10 illustrates a communications system 1000 including the aerosol delivery device 900. The communication interface may be configured to enable establishment of or connection to a computing device 1002 external to the aerosol delivery device (an external computing device). This computing device may also be embodied as a number of different devices, such as any of a number of different mobile computers. More particular examples of suitable mobile computers include portable computers (e.g., laptops, notebooks, tablet computers), mobile phones (e.g., cell phones, smartphones), wearable computers (e.g., smartwatches) and the like. In other examples, the computing device may be embodied as other than a mobile computer, such as in the manner of a desktop computer, server computer or the like. In yet other examples, the computing device may be embodied as another aerosol delivery device.

Additionally or alternatively, in some examples, the communication interface 924 of the aerosol delivery device 900 is configured to enable establishment of or connection to a wireless personal area network (WPAN) 1004 that includes the computing device 1002. Examples of suitable WPAN technologies include those based on or specified by IEEE 802.15 standards, including Bluetooth, Bluetooth Low Energy (Bluetooth LE), ZigBee, infrared (e.g., IrDA), radio-frequency identification (RFID), Wireless USB and the like. In some examples, then, the processing circuitry 906 may be configured to enable half-duplex Bluetooth Low Energy communication with the computing device via the wireless communication interface. Other examples of suitable WPAN technologies include Wi-Fi Direct, as well as certain other technologies based on or specified by IEEE 802.11 standards and that support direct device-to-device communication.

In some examples, the communication interface 924 of the aerosol delivery device 900 may be configured to enable connection to a wireless local area network (WLAN) 1006. Examples of suitable WLAN technologies include those based on or specified by IEEE 802.11 standards and marketed as Wi-Fi. The WLAN includes appropriate networking hardware, some of which may be integral and others of which may be separate and interconnected. As shown, for example, the WLAN includes a wireless access point 1008 configured to permit wireless devices including the aerosol delivery device 900 and computing device 1002 to connect to the WLAN. As also shown, for example, the WLAN may include a gateway device 1010 such as a residential gateway configured to connect the WLAN to an external computer network 1012 such as a wide area network (WAN) like the Internet. In some examples, the wireless access point or gateway device may include an integrated router to which other systems or devices may be connected. The WLAN may also include other integral or separate and connected networking hardware, such as a network switch, hub, digital subscriber line (DSL) modem, cable modem or the like.

In some examples, the system 1000 may further include a service platform 1014, which may be embodied as a computer system accessible by the WLAN 1006 or external network 1012 (as shown). The service platform may include one or more servers, such as may be provided by one or more blade servers, a cloud computing infrastructure, distributed database or the like. In some examples, the service platform is embodied as a distributed computing apparatus including multiple computing devices, such as may be used to provide a cloud computing infrastructure or distributed database. One example of a suitable distributed database is a blockchain, which is a shared, immutable ledger for recording transactions. And in these examples, the computing devices that form the service platform may be in communication with each other via a network such as the external network.

In some examples, the service platform 1014 is accessible by the aerosol delivery device 900 over the WLAN 1006 and external network 1012, and configured to provide one or more services for a user of the aerosol delivery device and perhaps the users of other aerosol delivery devices. For example, the service platform may be operated by a retailer of aerosol delivery devices or components of aerosol delivery devices, aerosol precursor composition or the like. The service platform may enable a user to order or reorder aerosol precursor composition, access and use various features such as for monitoring, tracking or communicating a machine learning model, user profile or information derived from a machine learning model, user profile, or the like (described in greater detail below). In this regard, the service platform may store the machine learning model and/or user profile and enable the user to transfer either or both the machine learning model or user profile between different aerosol delivery devices. Or the aerosol delivery device may be capable of device-to-device transfer from one aerosol delivery device to another aerosol delivery device (e.g., computing device 1002 embodied as an aerosol delivery device).

Similar to the aerosol delivery device 900, in some examples, the service platform 1014 may be accessible by the computing device 1002 over the WLAN 1006 and external network 1012, although the WLAN or external network may be different between the aerosol delivery device and computing device. The computing device may include or otherwise provide an installed application or other interface through which the service platform may be accessible. This application or other interface may be or may be provided by a thin client and/or other client application, such as a web browser application through which a web page (e.g., service portal) provided by the service platform may be accessible. As another example, the application or other interface may be or may be provided by a dedicated application, such as a mobile app installed on a computing device embodied as a mobile computing device.

Referring back to FIG. 9 and with further reference to FIG. 10, in examples in which the aerosol delivery device 900 includes the camera system with digital camera 922, the digital camera may be configured to capture an image of a face (facial image) of an attempted user of the aerosol delivery device. In these examples, the processing circuitry 906 may be configured to perform a facial recognition using the facial image to verify the attempted user is an authorized user of the aerosol delivery device. The processing circuitry may be configured to then control at least one functional element of the aerosol delivery device based on verification of the attempted user. This may include the processing circuitry configured to alter a locked state of the aerosol delivery device based on verification of the attempted user.

The aerosol delivery device 900 may be configured to communicate with the service platform 1014 to carry out the facial recognition, or the aerosol delivery device may carry out the facial recognition locally without the service platform. In the latter example, the processing circuitry 906 may be configured to perform nodal analytics (sometimes referred to as node analytics) in which analytical computation of the facial image is performed locally at the aerosol delivery device. The facial recognition may therefore be performed without storing the facial image, with computation done rapidly and contours stored in onboard memory. The nodal analytics may consume less computational power and enable facial recognition with reduced latency. The nodal analytics may also enhance security and use less power at the aerosol delivery device.

In some examples, the processing circuitry 906 may be configured to perform the nodal analytics in response to a visual event, such as an attempted user appearing in the field of view of the digital camera 922. In response, the digital camera may capture a an image of the face of the attempted user, and the processing circuitry 906 may be configured to locally perform facial recognition using the image to verify the attempted user is an authorized user of the aerosol delivery device, without access to the service platform 1014.

The processing circuitry 906 may perform facial recognition in any of a number of different manners. In some examples, the processing circuitry may be trained to recognize the face of the authorized user using one or more reference images of the authorized user, which may define a training set for the facial recognition. This training may result in at least a threshold accuracy in verifying the authorized user, and may be performed before the facial recognition is used to control functional element(s) of the aerosol delivery device 900, such as the locked state of the aerosol delivery device. In some further examples, an initial training may be performed to achieve at least the threshold accuracy, and then may continue as the facial recognition is performed, with verified images of the authorized user being added in the training set for the facial recognition.

In some examples, the facial image may be divided into a number of points (e.g., 100 points) that can be used to verify the attempted user is an authorized user. The processing circuitry 906 may also include object recognition logic to distinguish an image of a face from an image of another object. This may help localize the process and reduce latency or computation error relative to techniques that involve at least some of the analysis being performed remote from the aerosol delivery device 900.

The digital camera 922 may be or include a linear imager to capture the facial image, or the digital camera may be or include a logarithmic imager. In comparison to a linear imager, a logarithmic imager may be capable of providing a higher dynamic range for image processing, in addition to reduced dependence on luminosity changes, which may occur due to shadows, reflections and the like. This may improve image capture, which may in turn improve analysis of the image.

A linear imager typically uses a pixel that generates a voltage as a linear function of light, which can result in a limited contrast. Contrast in a linear imager may also be dependent on luminosity, which can introduce reflection-based contrast issues. A logarithmic imager may reduce if not eliminate these issues. In a logarithmic imager, a pixel generates a voltage as a logarithmic function of light, which may improve contrast. The logarithmic imager may also provide a wider range of light levels and thus increased contrast due to the pixel voltage being logarithmically generated. In locations where shadows are generated or that have cloud cover, the logarithmic imager may be more beneficial than a linear imager. A logarithmic imager may also be beneficial when there is undue reflection on a person due to head lights or a sudden flash of light.

In addition to or in lieu of facial recognition, the aerosol delivery device 900 may be equipped with other machine learning functionality. In accordance with some example implementations, the processing circuitry 906 may be configured to record data for a plurality of uses of the aerosol delivery device. For each use, the data may include measurements of properties from the sensors 916, including the first sensor **916*a* and/or second sensor(s) 916*b***. The processing circuitry may then be configured to build a machine learning model to predict a target variable, and deploy the machine learning model to predict the target variable, and control at least one functional element of the aerosol delivery device based thereon. In this regard, the machine learning model may be built using a machine learning algorithm, at least one feature selected from the properties, and a training set produced from the measurements of the properties.

In some examples, the plurality of uses of the aerosol delivery device 900 may include respective user puffs each of which causes a flow of air through at least a portion of the housing of the aerosol delivery device, and is for user inhalation of the aerosol. In some of these examples, the processing circuitry 906 may be configured to the measurements of properties from the sensors 916 with times and durations of the respective user puffs. The times and durations may in some examples be provided or otherwise determined from a real-time clock (RTC) in the processing circuitry or accessible by the processing circuitry.

The target variable may be any of a number of different variables for different applications or use cases. The target variable may be a measure of health of the user, based on the measure of activity, and further based on a usage rate that depends on the times and durations of the respective user puffs. In some examples, the target variable may be or include a user profile that depends on at least one of the properties, and the times and durations of the respective user puffs.

In some examples, the user profile may include information that indicates a predicted period of non-use of the aerosol delivery device 900. In some of these examples, control of the functional element(s) of the aerosol delivery device may include the processing circuitry 906 configured to cause the aerosol delivery device to enter a sleep mode during the predicted period of non-use. The sleep mode may be a low-power or power-saving mode in which power may be cut to components such as first sensor **916*a*, which may not be needed during a period of non-use. In some examples, this mode may include powering components that may be used in charging the power source 908** of the aerosol delivery device, which may be particularly useful in cases in which the power source is rechargeable from a wireless RF based charger.

As indicated above and described in greater detail below, the user profile may depend on the respective user puffs. In this regard, the user profile may include or otherwise define a puff profile of the user. The puff profile may describe the respective user puffs. The puff profile may include the times and durations of the respective user puffs. Additionally or alternatively, the puff profile may include any of the properties that are characteristic of or otherwise relate to the respective user puffs. As described below, for example, this may include measurements of pressure that are proportional to strength of the respective user puffs, measurements of pressure that are proportional to total particular matter (TPM) in the aerosol produced during the respective user puffs, power dissipated by the aerosol production component during the respective puffs, the aerosol precursor composition used during the respective user puffs, the geographic position of the aerosol delivery device during the respective puffs, or the like. For other examples of properties that may be incorporated into the puff profile, see GB Pat. App. Ser. No. 1818007.5, filed Nov. 5, 2018, which is incorporated by reference herein.

In some examples, the property or properties on which the user profile depends may include the measurements of pressure from the first sensor **916*a*** that are proportional to strength of the respective user puffs. In other examples, the property or properties on which the user profile depends may include the measurements of pressure that are proportional to TPM in the aerosol produced during the respective user puffs.

In some further examples in which the target variable is or includes a user profile, the control of the functional element(s) may include the processing circuitry configured to control power from the power source 908 to the load 918 including the aerosol production component 910 based on the user profile.

In yet further examples the aerosol production component 910 includes a plurality of meshes surrounded by piezoelectric or piezomagnetic material (e.g., piezoelectric/piezomagnetic mesh of nozzle 820). In some of these examples, the processing circuitry 906 may be configured to selectively drive the piezoelectric or piezomagnetic material to vibrate and cause a discharge of components of the aerosol precursor composition through one or more of the meshes. In this regard, the processing circuitry may be configured to control power from the power source 908 to selectively drive the piezoelectric or piezomagnetic material based on the user profile.

In a particular example, the aerosol production component 910 includes three meshes operable to vibrate at respectively 113 kilohertz (kHz), 800 kHz and 2.2 megahertz, with the higher frequency forming smaller droplets of aerosol precursor composition. If the user frequently uses the aerosol delivery device 900, the processing circuitry 906 may drive all the three meshes. If the user less frequently uses the aerosol delivery device, less than the three may be driven. At the low end, the 113 kHz mesh may be driven, which may form larger droplets than the other two meshes. In some users, the larger droplets may not be completely ingested, which may facilitate a user decreasing usage of the device.

In some examples in which the second sensor(s) 916*b* include a current or voltage sensor, the current or voltage sensor may be configured to produce measurements of current through or voltage across the aerosol production component 910. In some of these examples, the processing circuitry 906 may be further configured to determine power dissipated by the aerosol production component during the respective user puffs based on the measurements of current through or voltage across the aerosol production component.

circuitry may be configured to determine resistivity of the aerosol precursor composition, and then identify the aerosol precursor composition from its resistivity.

In some of the above examples, the user profile may depend on at least the respective ones of the plurality of aerosol precursor compositions identified by the processing circuitry 906, and the times and durations of the respective user puffs when the aerosol delivery device is used therewith. In some further examples, the aerosol production component 910 may be a plurality of aerosol production components configured to produce aerosol from the plurality of aerosol precursor compositions. In some of these examples, control of the functional element(s) may include the processing circuitry configured to automatically select among the plurality of aerosol production components at different times based on the user profile.

In other further examples, the processing circuitry 906 may be further configured to predict depletion of a particular one of the plurality of aerosol precursor compositions based on the user profile. In some of these examples, control of the functional element(s) may include the processing circuitry 906 configured to communicate with the computing device 1002 or service platform 1014 via the communication interface 924 (e.g., wireless communication interface) to order an additional amount of the particular one of the plurality of aerosol precursor compositions.

To further illustrate some of the above examples, consider the case of four aerosol precursor compositions of different flavors (with different flavorants): Menthol, Crema, Chai and Tropicana. The user profile may include measurements of times and durations of use of the different flavors. The processing circuitry may apply regression principles to the measurements over a period of time (e.g., 30 days), and determine a boundary condition. Or in some examples, the processing circuitry may upload the measurements to the service platform 1014, which may determine the boundary condition.

|  | Coef | Standard Error | t Stat | P-value | Upper 95% | Lower 95% |
| --- | --- | --- | --- | --- | --- | --- |
| Intercept | 237987.8 | 72998.89 | 3.260157 | 0.008572 | 400639.5 | 75336.17 |
| Menthol | 16.80558 | 2.757692 | 6.094075 | 0.000117 | 22.9501 | 10.66106 |
| Crema | 11.74622 | 4.582404 | 2.563332 | 0.028211 | 21.95646 | 1.535992 |
| Chai | 17.79363 | 3.511406 | 5.067379 | 0.000487 | 25.61753 | 9.969726 |
| Tropicana | 0.174306 | 3.847821 | 0.0453 | 0.96476 | 8.747787 | −8.39917 |

Also in some of these examples, the property or properties on which the user profile depends may include the power dissipated by the aerosol production component during the respective user puffs.

In some examples, the aerosol delivery device 900 may be usable with at least a plurality of aerosol precursor compositions, and the second sensor(s) 916*b* may include a reader configured to read machine-readable information. From this machine-readable information, the processing circuitry 906 may be configured to identify respective ones of the plurality of aerosol precursor compositions during the respective user puffs when the aerosol delivery device is used therewith.

The plurality of aerosol precursor compositions may have different resistivities, which may also be used to identify respective ones of the plurality. In some examples in which the second sensor(s) 916*b* include a resistance sensor, the resistance sensor may be a sensor configured to produce a measurement of resistance of the aerosol precursor composition. From this measure of resistance, then, the processing From the boundary condition, it may be understood that the user prefers Menthol and Chai, and this understanding may be used to deliver or otherwise provide more of those flavors to the user. The service platform 1014 in particular may be accessible by a marketing team to supply more of those flavors more frequently used by the user—or over larger numbers of users.

In some examples, the processing circuitry 906 may be configured to communicate the target variable to the service platform 1014 via the wireless communication interface 924, the service platform configured to electronically record the target variable on a blockchain. Those with access to the blockchain may thereby access the target variable. The predicted target variable may be compared with actual data for the target variable. As the predicted and actual converge, the system 1000 may predict the actual data and thus increase efficiency of the system using machine learning and blockchain.

In some examples in which the second sensor(s) 916*b* include a position sensor configured to determine a geographic position of the aerosol delivery device, the property or properties on which the user profile depends may include the geographic position of the aerosol delivery device during the respective user puffs. In other examples, the computing device 1002 may include a position sensor (in addition to or in lieu of the aerosol deliver device) configured to determine the geographic position of the computing device. When the aerosol delivery device is in proximity of the computing device, the geographic position of the computing device may approximate the geographic position of the aerosol delivery device. The computing device may communicate the geographic position to the aerosol delivery device via the communication interface 924 (e.g., wireless communication interface) for use similar to the geographic position determined by a position sensor of the aerosol delivery device.

By way of further example, the user profile may include information that indicates one or more predicted geographic areas of use or non-use of the aerosol delivery device, predicted based on geographic positions of the aerosol delivery device 900 (or computing device 1002 in proximity of the aerosol delivery device). In some of these examples, control of the functional element(s) of the aerosol delivery device may include the processing circuitry 906 configured to cause the aerosol delivery device to unlock when the aerosol delivery device is located within a predicted geographic area of use, or lock when the aerosol delivery device is located outside the predicted geographic area(s) of use or within a predicted geographic area of non-use. In this regard, the aerosol delivery device may learn where the authorized user uses or does not use the device, and lock or unlock the device based on that information, which may prevent unauthorized use such as in the case of a lost or stolen aerosol delivery device.

In others of the above examples involving predicted geographic area(s) of use or non-use, control of the functional element(s) of the aerosol delivery device 900 may include the processing circuitry 906 configured to prepare the aerosol delivery device for usage when approaching or within a predicted geographic area of use. This may include restoring the aerosol delivery device from sleep mode or otherwise activating components to which power may have been cut such as first sensor 916a. Additionally or alternatively, in some examples in which the aerosol production component 910 is or includes a heating element, the processing circuitry may initiate a pre-heat of the heating element. Conversely, the processing circuitry may be configured to cause the aerosol delivery device to enter the sleep mode when the aerosol delivery device exits or is located outside the predicted geographic area(s) of use, or approaches or within a predicted geographic area of non-use.

In some further examples, the user profile may include information that indicates one or more predicted geographic areas of modified use of the aerosol delivery device, predicted based on geographic positions of the aerosol delivery device 900 (or computing device 1002 in proximity of the aerosol delivery device). In some of these examples, control of the functional element(s) of the aerosol delivery device may include the processing circuitry 906 configured to cause the aerosol delivery device to adjust the volume of aerosol produced by the aerosol delivery device when the aerosol delivery device is located within a predicted geographic area of modified use. In particular, for example, the aerosol delivery device may decrease the volume of aerosol produced by the aerosol delivery device when the aerosol delivery device is indoors or in another geographic area where modified use is desired.

Like predicted geographic area(s) of use (or modified use), other aspects of the user profile may be used to lock the aerosol delivery device 900 to the authorized user. As described above, the user profile may include or otherwise define a puff profile of the authorized user, which may describe respective user puffs of the user. In some examples, the aerosol delivery device may be locked to the puff profile of the authorized user. In these examples, the processing circuitry 906 may develop a use-specific puff profile of respective puffs during a use of the aerosol delivery device, and compare the use-specific puff profile to the puff profile within the user profile. The processing circuitry may enable continued use when the use-specific puff profile and puff profile match or otherwise have at least a threshold similarity, and lock the aerosol delivery device from continued use when the use-specific puff profile and puff profile do not match or otherwise have at least the threshold similarity.

In another, similar example, the processing circuitry 906 may use the puff profile to distinguish between users over or under a permitted age for use of the aerosol delivery device 900. Here the processing circuitry may enable continued use when the use-specific puff profile indicates the user is at least the permitted age, and lock the aerosol delivery device from continued use when the use-specific puff profile indicates the user is not at least the permitted age.

In some examples, the aerosol delivery device 900 is configured to communicate with a second aerosol delivery device (e.g., computing device 1002 embodied as an aerosol delivery device) via the communication interface 924 (e.g., wireless communication interface). In some of these examples, the aerosol delivery device may be configured to receive, from the second aerosol delivery device, second measurements of the properties during use of the second aerosol delivery device that includes respective second user puffs, and second times and durations of the respective second user puffs. The processing circuitry 906 may be further configured to build and deploy a second machine learning model to predict a second target variable. The second machine learning model may be built using the machine learning algorithm, the at least one feature selected from the properties, and a second training set produced from the second measurements of the properties. Here, the second target variable may be a second user profile that depends on the at least one of the properties, and the second times and durations of the respective second user puffs.

In the above examples, a user may pair their aerosol delivery device 900 with the aerosol delivery device of another user. This may allow the user to monitor usage of the user and other user, such as times, frequency, aerosol precursor composition and the like, which may produce somewhat of a social network. There may further be more than two aerosol delivery devices to provide a larger social network in which each user may monitor usage of users of the devices in the social network. In these and other examples, the aerosol delivery device may additionally or alternatively upload usage information to the service platform 1024. For more information on suitable social networking features, see U.S. Pat. App. Pub. No. 2015/0224268 to Henry et al., which is incorporated herein by reference.

In some examples in which the second sensor(s) 916b include an accelerometer, the accelerometer may be configured to produce measurements of acceleration of the aerosol delivery device 900, and the target variable may be a logical activity of a user of the aerosol delivery device. In some of these examples, the machine learning model may be or include an activity detection model to predict the logical activity of the user. And the processing circuitry 906 may be configured to build the activity detection model using the machine learning algorithm, the at least one feature that includes the acceleration, and the training set produced from the measurements of acceleration.

In other examples in which the second sensor(s) 916*b* include an accelerometer, the target variable may be a logical carry position of the aerosol delivery device 900. In some of these examples, the machine learning model may be or include a carry position detection model to predict the logical carry position of the aerosol delivery device. And the processing circuitry 906 may be configured to build the carry position detection model using the machine learning algorithm, the at least one feature that includes the acceleration, and the training set produced from the measurements of acceleration.

In other examples in which the second sensor(s) 916*b* include an accelerometer, the target variable may be a gesture performed using the aerosol delivery device 900. In some of these examples, the machine learning model may be or include a gesture recognition model to predict the gesture. And the processing circuitry 906 may be configured to build the gesture recognition model using the machine learning algorithm, the at least one feature that includes the acceleration, and the training set produced from the measurements of acceleration.

In the above and other similar examples, the processing circuitry 906 may be configured to control functional element(s) of the aerosol delivery device 900 based on the as-predicted logical activity of the user, logical carry position of the aerosol delivery device, gesture, or the like. When the logical activity, carry position or gesture indicate use of the aerosol delivery device, for example, the processing circuitry may restore the aerosol delivery device from sleep mode or otherwise activate components to which power may have been cut such as first sensor 916*a*. Additionally or alternatively, in some examples in which the aerosol production component 910 is or includes a heating element, the processing circuitry may initiate a pre-heat of the heating element.

In some examples, the user profile may include information that describes the authorized user by one or more logical activities, carry positions and/or gestures may be used to describe the authorized user, similar to the puff profile of the authorized user. In these examples, this information may be used to lock the aerosol delivery device 900 to the authorized user, in addition to or in lieu of the puff profile. The processing circuitry 906 may predict logical activity, carry position and/or gesture during a use of the aerosol delivery device, and compare the predicted logical activity, carry position and/or gesture to the information in the user profile. The processing circuitry may enable continued use when the predicted logical activity, carry position and/or gesture matches or otherwise has at least a threshold similarity with the information in the user profile, and lock the aerosol delivery device from continued use when the predicted logical activity, carry position and/or gesture and information in the user profile do not match or otherwise have at least the threshold similarity.

In yet other examples in which the second sensor(s) 916*b* include an accelerometer, the target variable may be or may be based on a measure of activity of a user of the aerosol delivery device 900 that is proportional to a count of steps of the user. The count of steps may be determinable from the measurements of acceleration. In some of these examples, the processing circuitry may be configured to build the machine learning model to predict the measure of activity of the user. Here, the model may be built using the machine learning algorithm, the at least one feature that includes the acceleration, and the training set produced from the measurements of acceleration. The steps may be used to determine rate of use of the aerosol delivery device versus activity. If the rate of use goes up and the measure of activity goes down, the processing circuitry 906 may trigger a visual, tactile and/or sound indicator to encourage the user to increase their activity.

In some examples in which the second sensor(s) 916*b* include a resistance sensor, the resistance sensor may be a sensor configured to produce measurements of resistance of the aerosol precursor composition. The target variable may be a measure of quality of the aerosol precursor composition that is proportional to a resistivity of the aerosol precursor composition, and the resistivity may be determinable from the measurements of resistance. Here, the machine learning model may be or include a machine learning model to predict the measure of quality of the aerosol precursor composition. The processing circuitry 906 may be configured to build the machine learning mode model using the machine learning algorithm, the at least one feature that includes the resistance of the aerosol precursor composition, and the training set produced from the measurements of resistance.

In particular, consider an example implementation in which the aerosol production component 910 is or includes a heating element to heat a liquid aerosol precursor composition that includes polyhydric alcohol. As the heating element heats the aerosol precursor composition, the amount of the polyhydric alcohol may be reduced, which may likewise reduce the quality of the aerosol precursor composition. It may also reduce resistivity of the aerosol precursor composition. Given a baseline resistivity for aerosol precursor composition, measurements of resistance may be made during use of the aerosol delivery device 900, resistivity of the aerosol precursor composition may be determined and compared to the baseline resistivity to determine quality of remaining aerosol precursor composition.

In some examples in which the power source 908 is rechargeable, the data for the plurality of uses includes a count and frequency of recharges of the power source. In some of these examples, the target variable may be a measure of life expectancy of the aerosol precursor composition or the power source that is proportional to the count and frequency of recharges of the power source. The processing circuitry 906 may be configured to build the machine learning model to predict the measure of life expectancy of the aerosol precursor composition or the power source, using the machine learning algorithm, the at least one feature that includes the count and frequency of recharges of the power source, and the training set produced from the count and frequency of recharges.

In the above, machine learning and perhaps a fuel gauge may be used to anticipate life expectancy of the power source 908. If the user frequently uses and recharges the power source, anticipated life expectancy of the power source may be measured as a function of usage. If the usage is low, the power source may have a higher anticipated life expectancy. In some examples a fuel gauge may not be used, and an expected life expectancy in number of charges relative to a current count of charges may be used.

In some examples in which the measure of life expectancy of the power source 908 is predicted, control of the functional element(s) of the aerosol delivery device 900 may include the processing circuitry 906 configured to cause the aerosol delivery device to enter a sleep mode when the measure of life expectancy decreases below a threshold time, similar to when the aerosol delivery device is not needed during a period of non-use. Or the processing circuitry may cause the aerosol delivery device to enter a different power-saving mode in which power remains to components required for use of the device to produce aerosol, but in which power may be cut to other components.

In some examples in which the second sensor(s) 916b include microphones, the microphones may be configured to produce measurements of audio from an audio source in an environment of the aerosol delivery device 900. In some of these examples, the processing circuitry 906 may be further configured to create a virtual directional microphone having a beam pattern created from the measurements of audio, and that points in a direction of the audio source.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-10 or as otherwise described above may be included in an aerosol delivery device according to the present disclosure.

Many modifications and other implementations of the disclosure will come to mind to one skilled in the art to which this disclosure pertains having the benefit of the teachings presented in the foregoing descriptions and the associated figures. Therefore, it is to be understood that the disclosure is not to be limited to the specific implementations disclosed herein and that modifications and other implementations are intended to be included within the scope of the appended claims. Although specific terms are employed herein, they are used in a generic and descriptive sense only and not for purposes of limitation.

What is claimed is:

1. An aerosol delivery device comprising:

a housing structured to retain an aerosol precursor composition;

at least one sensor configured to produce measurements of properties during use of the aerosol delivery device;

a power source;

an aerosol production component configured to produce an aerosol from the aerosol precursor composition; and a control component including processing circuitry configured to:

switchably connect the power source to a load including the aerosol production component and thereby power the aerosol production component, record data for a plurality of uses of the aerosol delivery device, for each use of which the data includes the measurements of the properties, build a machine learning model to predict a target variable, the machine learning model built using a machine learning algorithm, at least one feature selected from the properties, and a training set produced from the measurements of the properties, deploy the machine learning model to predict the target variable, and control at least one functional element of the aerosol delivery device based thereon, and verify that an attempted user is authorized to use the aerosol delivery device, wherein the processing circuitry being configured to control the at least one functional element includes being configured to alter a locked state of the aerosol delivery device based on the verifying of the attempted user;

wherein the plurality of uses of the aerosol delivery device includes respective user puffs each of which causes a flow of air through at least a portion of the housing, and is for user inhalation of the aerosol, and wherein the processing circuitry being configured to record the data for the plurality of uses includes being configured to record the measurements with times and durations of the respective user puffs.

2. The aerosol delivery device of claim 1 further comprising a camera system including a digital camera configured to capture an image of a face of the attempted user of the aerosol delivery device, wherein the processing circuitry is configured to perform a facial recognition using the image to verify the attempted user is authorized to use the aerosol delivery device, and the processing circuitry being configured to control the at least one functional element includes being configured to alter a locked state of the aerosol delivery device based on the verifying of the attempted user.

3. The aerosol delivery device of claim 1, wherein the target variable is a user profile that depends on at least one of the properties, and the times and durations of the respective user puffs.

4. The aerosol delivery device of claim 3, wherein the user profile includes information that indicates a predicted period of non-use of the aerosol delivery device, and the processing circuitry being configured to control the at least one functional element includes being configured to cause the aerosol delivery device to enter a sleep mode during the predicted period of non-use.

5. The aerosol delivery device of claim 3, wherein the processing circuitry being configured to control the at least one functional element includes being configured to control power from the power source to the load including the aerosol production component based on the user profile.

6. The aerosol delivery device of claim 5, wherein the aerosol production component includes a plurality of meshes surrounded by piezoelectric or piezomagnetic material, the processing circuitry configured to selectively drive the piezoelectric or piezomagnetic material to vibrate and cause a discharge of components of the aerosol precursor composition through one or more of the meshes, and wherein the processing circuitry being configured to control power from the power source includes being configured to control power from the power source to selectively drive the piezoelectric or piezomagnetic material based on the user profile.

7. The aerosol delivery device of claim 3, wherein the at least one sensor includes a pressure sensor configured to produce measurements of pressure caused by the flow of air, and the at least one of the properties on which the user profile depends includes the measurements of pressure that are proportional to strength of the respective user puffs.

8. The aerosol delivery device of claim 3, wherein the at least one sensor includes a pressure sensor configured to produce measurements of pressure caused by the flow of air that are proportional to total particular matter (TPM) in the aerosol produced during the respective user puffs, and the at least one of the properties on which the user profile depends includes the measurements of pressure that are proportional to TPM in the aerosol produced during the respective user puffs.

9. The aerosol delivery device of claim 3, wherein the at least one sensor includes a current or voltage sensor configured to produce measurements of current through or voltage across the aerosol production component, and the processing circuitry is further configured to determine power dissipated by the aerosol production component during the respective user puffs based on the measurements of current through or voltage across the aerosol production component, and wherein the at least one of the properties on which the user profile depends includes the power dissipated by the aerosol production component during the respective user puffs.

10. The aerosol delivery device of claim 3, wherein the aerosol delivery device is usable with at least a plurality of aerosol precursor compositions, and the at least one sensor includes a reader configured to read machine-readable information from which the processing circuitry is configured to identify respective ones of the plurality of aerosol precursor compositions during the respective user puffs when the aerosol delivery device is used therewith, and wherein the user profile depends on at least the respective ones of the plurality of aerosol precursor compositions identified by the processing circuitry, and the times and durations of the respective user puffs when the aerosol delivery device is used therewith.

11. The aerosol delivery device of claim 10, wherein the aerosol production component is a plurality of aerosol production components configured to produce aerosol from the plurality of aerosol precursor compositions, and wherein the processing circuitry being configured to control the at least one functional element includes being configured to automatically select among the plurality of aerosol production components at different times based on the user profile.

12. The aerosol delivery device of claim 10, wherein the processing circuitry is further configured to predict depletion of a particular one of the plurality of aerosol precursor compositions based on the user profile, and wherein the aerosol delivery device further comprises a wireless communication interface, and the processing circuitry being configured to control the at least one function element includes being configured to communicate with a computing device or a service platform via the wireless communication interface to order an additional amount of the particular one of the plurality of aerosol precursor compositions.

13. The aerosol delivery device of claim 3, wherein the at least one sensor includes a position sensor configured to determine a geographic position of the aerosol delivery device, and the at least one of the properties on which the user profile depends includes the geographic position of the aerosol delivery device during the respective user puffs.

14. The aerosol delivery device of claim 13, wherein the user profile includes information that indicates one or more predicted geographic areas of use or non-use of the aerosol delivery device, predicted based on the geographic positions of the aerosol delivery device during the user puffs, and the processing circuitry being configured to control the at least one functional element includes being configured to unlock the aerosol delivery device when the aerosol delivery device is located within a predicted geographic area of use, and being configured to lock the aerosol delivery device when the aerosol delivery device is located outside the predicted geographic area of use or is within a predicted geographic area of non-use.

15. The aerosol delivery device of claim 13, wherein the user profile includes information that indicates one or more predicted geographic areas of use or non-use of the aerosol delivery device, predicted based on the geographic positions of the aerosol delivery device during the user puffs, and the processing circuitry being configured to control the at least one functional element includes being configured to prepare the aerosol delivery device for use when approaching or within a predicted geographic area of use, wherein preparing includes restoring the aerosol delivery device from a sleep mode or activating components to which power is cut in the sleep mode, and being configured to cause the aerosol delivery device to enter the sleep mode when the aerosol delivery device exits or is located outside the predicted geographic area of use, or approaches or is within a predicted geographic area of non-use.

16. The aerosol delivery device of claim 13, wherein the user profile includes information that indicates one or more predicted geographic areas of modified use of the aerosol delivery device, predicted based on the geographic positions of the aerosol delivery device during the user puffs, and the processing circuitry being configured to control the at least one functional element includes being configured to cause the aerosol delivery device to adjust by increasing or decreasing a volume of aerosol produced by the aerosol delivery device when the aerosol delivery device is located within one of the predicted geographic area of modified use.

17. The aerosol delivery device of claim 3 further comprising a wireless communication interface via which the aerosol delivery device is configured to receive, from a second aerosol delivery device, second measurements of the properties during use of the second aerosol delivery device that includes respective second user puffs, and second times and durations of the respective second user puffs, wherein the processing circuitry is further configured to build and deploy a second machine learning model to predict a second target variable, the second machine learning model built using the machine learning algorithm, the at least one feature selected from the properties, and a second training set produced from the second measurements of the properties, the second target variable being a second user profile that depends on the at least one of the properties, and the second times and durations of the respective second user puffs.

18. The aerosol delivery device of claim 3, wherein the user profile includes or defines a puff profile of an authorized user of the aerosol delivery device, wherein the processing circuitry is configured to develop a use-specific puff profile of respective user puffs during a use of the aerosol delivery device, and compare the use-specific puff profile to the authorized user puff profile, and the processing circuitry being configured to control the at least one functional element includes being configured to enable continued use of the aerosol delivery device when the use-specific puff profile and authorized user puff profile match or have at least a threshold similarity, and being configured to lock the aerosol delivery device from continued use when the use-specific puff profile and authorized user puff profile do not match or have at least the threshold similarity.

19. The aerosol delivery device of claim 3, wherein the user profile includes or defines a threshold age of an authorized user associated with the authorized user puff profile, and the processing circuitry being configured to control the at least one functional element includes being configured to enable continued use of the aerosol delivery device when the use-specific puff profile indicates that the attempted user is at least the threshold age, and being configured to lock the aerosol delivery device from continued use when the use-specific puff profile indicates that the attempted user is not at least the threshold age.

20. The aerosol delivery device of claim 1, wherein the at least one sensor includes an accelerometer configured to produce measurements of acceleration of the aerosol delivery device, and the target variable is a logical activity of a user of the aerosol delivery device, and wherein the processing circuitry being configured to build the machine learning model includes being configured to build an activity detection model to predict the logical activity of the user, the activity detection model being built using the machine learning algorithm, the at least one feature that includes the acceleration, and the training set produced from the measurements of acceleration.

21. The aerosol delivery device of claim 1, wherein the at least one sensor includes an accelerometer configured to produce measurements of acceleration of the aerosol delivery device, and the target variable is a logical carry position of the aerosol delivery device, and wherein the processing circuitry being configured to build the machine learning model includes being configured to build a carry position detection model to predict the logical carry position of the aerosol delivery device, the carry position detection model being built using the machine learning algorithm, the at least one feature that includes the acceleration, and the training set produced from the measurements of acceleration.

22. The aerosol delivery device of claim 1, wherein the at least one sensor includes an accelerometer configured to produce measurements of acceleration of the aerosol delivery device, and the target variable is a gesture performed using the aerosol delivery device, and wherein the processing circuitry being configured to build the machine learning model includes being configured to build a gesture recognition model to predict the gesture, the gesture recognition model being built using the machine learning algorithm, the at least one feature that includes the acceleration, and the training set produced from the measurements of acceleration.

23. The aerosol delivery device of claim 1, wherein the at least one sensor includes microphones configured to produce measurements of audio from an audio source in an environment of the aerosol delivery device, and wherein the processing circuitry is further configured to create a virtual directional microphone having a beam pattern created from the measurements of audio, and that points in a direction of the audio source.

24. The aerosol delivery device of claim 1 further comprising a wireless communication interface, and wherein the processing circuitry is further configured to enable half-duplex Bluetooth Low Energy communication with a computing device via the wireless communication interface.

25. The aerosol delivery device of claim 1, wherein the at least one sensor includes a sensor configured to produce measurements of resistance of the aerosol precursor composition, and the target variable is a measure of quality of the aerosol precursor composition that is proportional to a resistivity of the aerosol precursor composition, and the resistivity is determinable from the measurements of resistance, and wherein the processing circuitry being configured to build the machine learning model includes being configured to build the machine learning model to predict the measure of quality of the aerosol precursor composition, the model being built using the machine learning algorithm, the at least one feature that includes the resistance of the aerosol precursor composition, and the training set produced from the measurements of resistance.

26. The aerosol delivery device of claim 1, wherein the power source is rechargeable, the data for the plurality of uses includes a count and frequency of recharges of the power source, and the target variable is a measure of life expectancy of the aerosol precursor composition or the power source that is proportional to the count and frequency of recharges of the power source, and wherein the processing circuitry being configured to build the machine learning model includes being configured to build the machine learning model to predict the measure of life expectancy of the aerosol precursor composition or the power source, the model being built using the machine learning algorithm, the at least one feature that includes the count and frequency of recharges of the power source, and the training set produced from the count and frequency of recharges.

27. The aerosol delivery device of claim 1, wherein the at least one sensor includes an accelerometer configured to produce measurements of acceleration of the aerosol delivery device, and the target variable is or is based on a measure of activity of a user of the aerosol delivery device that is proportional to a count of steps of the user, and the count of steps is determinable from the measurements of acceleration, and wherein the processing circuitry being configured to build the machine learning model includes being configured to build the machine learning model to predict the measure of activity of the user, the model being built using the machine learning algorithm, the at least one feature that includes the acceleration, and the training set produced from the measurements of acceleration.

28. The aerosol delivery device of claim 27, wherein the plurality of uses of the aerosol delivery device includes respective user puffs each of which causes a flow of air through at least a portion of the housing, and is for user inhalation of the aerosol, and wherein the processing circuitry being configured to record the data for the plurality of uses includes being configured to record the measurements with times and durations of the respective user puffs, and the target variable is a measure of health of the user, based on the measure of activity, and further based on a usage rate that depends on the times and durations of the respective user puffs.

29. The aerosol delivery device of claim 1 further comprising a wireless communication interface, wherein the processing circuitry being configured to control the at least one function element includes being configured to communicate the target variable to a service platform via the wireless communication interface, the service platform configured to electronically record the target variable on a blockchain.

30. An aerosol delivery device comprising:
an aerosol precursor composition;
at least one sensor configured to produce measurements of properties during use of the aerosol delivery device;
a power source;
an aerosol production component configured to produce an aerosol from the aerosol precursor composition; and
a control component including processing circuitry configured to:
switchably connect the power source to a load including the aerosol production component and thereby power the aerosol production component,
record data for a plurality of uses of the aerosol delivery device, for each use of which the data includes the measurements of the properties, build a machine learning model to predict a target variable, the machine learning model built using a machine learning algorithm, at least one feature selected from the properties, and a training set produced from the measurements of the properties, and deploy the machine learning model to predict the target variable, and control at least one functional element of the aerosol delivery device based thereon, wherein the processing circuitry being configured to record the data for the plurality of uses includes being configured to record the measurements with times and durations of the respective user puffs, and the target variable is a user profile that depends on at least one of the properties, and the times and durations of the respective user puffs, and wherein the user profile includes information that indicates a predicted period of non-use of the aerosol delivery device, and the processing circuitry being configured to control the at least one functional element includes being configured to cause the aerosol delivery device to enter a sleep mode during the predicted period of non-use.

31. An aerosol delivery device comprising:

an aerosol precursor composition;

at least one sensor configured to produce measurements of properties during use of the aerosol delivery device;

a power source;

an aerosol production component configured to produce an aerosol from the aerosol precursor composition; and a control component including processing circuitry configured to:

switchably connect the power source to a load including the aerosol production component and thereby power the aerosol production component, record data for a plurality of uses of the aerosol delivery device, for each use of which the data includes the measurements of the properties, build a machine learning model to predict a target variable, the machine learning model built using a machine learning algorithm, at least one feature selected from the properties, and a training set produced from the measurements of the properties, and deploy the machine learning model to predict the target variable, and control at least one functional element of the aerosol delivery device based thereon, wherein the processing circuitry being configured to record the data for the plurality of uses includes being configured to record the measurements with times and durations of the respective user puffs, and the target variable is a user profile that depends on at least one of the properties, and the times and durations of the respective user puffs, and wherein the user profile includes or defines a puff profile of an authorized user of the aerosol delivery device, wherein the processing circuitry is configured to develop a use-specific puff profile of respective user puffs during a use of the aerosol delivery device, and compare the use-specific puff profile to the authorized user puff profile, and the processing circuitry being configured to control the at least one functional element includes being configured to enable continued use of the aerosol delivery device when the use-specific puff profile and authorized user puff profile match or have at least a threshold similarity, and being configured to lock the aerosol delivery device from continued use when the use-specific puff profile and authorized user puff profile do not match or have at least the threshold similarity.

32. An aerosol delivery device comprising:

an aerosol precursor composition;

at least one sensor configured to produce measurements of properties during use of the aerosol delivery device;

a power source;

an aerosol production component configured to produce an aerosol from the aerosol precursor composition; and a control component including processing circuitry configured to:

switchably connect the power source to a load including the aerosol production component and thereby power the aerosol production component, record data for a plurality of uses of the aerosol delivery device, for each use of which the data includes the measurements of the properties, build a machine learning model to predict a target variable, the machine learning model built using a machine learning algorithm, at least one feature selected from the properties, and a training set produced from the measurements of the properties, and deploy the machine learning model to predict the target variable, and control at least one functional element of the aerosol delivery device based thereon, wherein the processing circuitry being configured to record the data for the plurality of uses includes being configured to record the measurements with times and durations of the respective user puffs, and the target variable is a user profile that depends on at least one of the properties, and the times and durations of the respective user puffs, and wherein the user profile includes or defines a threshold age of an authorized user associated with the authorized user puff profile, and the processing circuitry being configured to control the at least one functional element includes being configured to enable continued use of the aerosol delivery device when the use-specific puff profile indicates that the attempted user is at least the threshold age, and being configured to lock the aerosol delivery device from continued use when the use-specific puff profile indicates that the attempted user is not at least the threshold age.

33. An aerosol delivery device comprising:

an aerosol precursor composition;

at least one sensor configured to produce measurements of properties during use of the aerosol delivery device;

a power source;

an aerosol production component configured to produce an aerosol from the aerosol precursor composition; and a control component including processing circuitry configured to:

switchably connect the power source to a load including the aerosol production component and thereby power the aerosol production component, record data for a plurality of uses of the aerosol delivery device, for each use of which the data includes the measurements of the properties, build a machine learning model to predict a target variable, the machine learning model built using a machine learning algorithm, at least one feature selected from the properties, and a training set produced from the measurements of the properties, and deploy the machine learning model to predict the target variable, and control at least one functional element of the aerosol delivery device based thereon, wherein the at least one sensor includes a position sensor configured to determine a geographic position of the aerosol delivery device, and the at least one of the properties on which the user profile depends includes the geographic position of the aerosol delivery device during the respective user puffs, and wherein the user profile includes information that indicates one or more predicted geographic areas of use or non-use of the aerosol delivery device, predicted based on the geographic positions of the aerosol delivery device during the user puffs, and the processing circuitry being configured to control the at least one functional element includes being configured to unlock the aerosol delivery device when the aerosol delivery device is located within a predicted geographic area of use, and being configured to lock the aerosol delivery device when the aerosol delivery device is located outside the predicted geographic area of use or is within a predicted geographic area of non-use, wherein the plurality of uses of the aerosol delivery device includes respective user puffs each of which causes a flow of air through at least a portion of the housing, and is for user inhalation of the aerosol, and wherein the processing circuitry being configured to record the data for the plurality of uses includes being configured to record the measurements with times and durations of the respective user puffs.

34. An aerosol delivery device comprising:
an aerosol precursor composition;
at least one sensor configured to produce measurements of properties during use of the aerosol delivery device;
a power source;
an aerosol production component configured to produce an aerosol from the aerosol precursor composition; and
a control component including processing circuitry configured to:
switchably connect the power source to a load including the aerosol production component and thereby power the aerosol production component,
record data for a plurality of uses of the aerosol delivery device, for each use of which the data includes the measurements of the properties,
build a machine learning model to predict a target variable, the machine learning model built using a machine learning algorithm, at least one feature selected from the properties, and a training set produced from the measurements of the properties, and
deploy the machine learning model to predict the target variable, and control at least one functional element of the aerosol delivery device based thereon,
wherein the at least one sensor includes a position sensor configured to determine a geographic position of the aerosol delivery device, and the at least one of the properties on which the user profile depends includes the geographic position of the aerosol delivery device during the respective user puffs, and
wherein the user profile includes information that indicates one or more predicted geographic areas of use or non-use of the aerosol delivery device, predicted based on the geographic positions of the aerosol delivery device during the user puffs, and the processing circuitry being configured to control the at least one functional element includes being configured to prepare the aerosol delivery device for use when approaching or within a predicted geographic area of use, wherein preparing includes restoring the aerosol delivery device from a sleep mode or activating components to which power is cut in the sleep mode, and being configured to cause the aerosol delivery device to enter the sleep mode when the aerosol delivery device exits or is located outside the predicted geographic area of use, or approaches or is within a predicted geographic area of non-use, wherein the plurality of uses of the aerosol delivery device includes respective user puffs each of which causes a flow of air through at least a portion of the housing, and is for user inhalation of the aerosol, and wherein the processing circuitry being configured to record the data for the plurality of uses includes being configured to record the measurements with times and durations of the respective user puffs.

35. An aerosol delivery device comprising:
an aerosol precursor composition;
at least one sensor configured to produce measurements of properties during use of the aerosol delivery device;
a power source;
an aerosol production component configured to produce an aerosol from the aerosol precursor composition; and
a control component including processing circuitry configured to:
switchably connect the power source to a load including the aerosol production component and thereby power the aerosol production component,
record data for a plurality of uses of the aerosol delivery device, for each use of which the data includes the measurements of the properties,
build a machine learning model to predict a target variable, the machine learning model built using a machine learning algorithm, at least one feature selected from the properties, and a training set produced from the measurements of the properties, and
deploy the machine learning model to predict the target variable, and control at least one functional element of the aerosol delivery device based thereon,
wherein the at least one sensor includes a position sensor configured to determine a geographic position of the aerosol delivery device, and the at least one of the properties on which the user profile depends includes the geographic position of the aerosol delivery device during the respective user puffs, and
wherein the user profile includes information that indicates one or more predicted geographic areas of modified use of the aerosol delivery device, predicted based on the geographic positions of the aerosol delivery device during the user puffs, and the processing circuitry being configured to control the at least one functional element includes being configured to cause the aerosol delivery device to adjust by increasing or decreasing a volume of aerosol produced by the aerosol delivery device when the aerosol delivery device is located within one of the predicted geographic area of modified use, wherein the plurality of uses of the aerosol delivery device includes respective user puffs each of which causes a flow of air through at least a portion of the housing, and is for user inhalation of the aerosol, and wherein the processing circuitry being configured to record the data for the plurality of uses includes being configured to record the measurements with times and durations of the respective user puffs.

* * * * *